(12) United States Patent
Escobedo et al.

(10) Patent No.: US 6,566,075 B1
(45) Date of Patent: May 20, 2003

(54) METHODS FOR DETECTING HUMAN PLATELET-DERIVED GROWTH FACTOR RECEPTOR AGONISTS AND ANTAGONISTS

(75) Inventors: Jaime A. Escobedo, Alamo, CA (US); Lewis T. Williams, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/628,188

(22) Filed: Jul. 28, 2000

Related U.S. Application Data

(60) Division of application No. 08/240,294, filed on May 9, 1994, now Pat. No. 6,110,737, which is a continuation of application No. 08/031,082, filed on Mar. 15, 1993, now abandoned, which is a continuation of application No. 07/771,829, filed on Oct. 7, 1991, now abandoned, which is a continuation of application No. 07/309,322, filed on Feb. 10, 1989, now abandoned, which is a continuation-in-part of application No. 07/151,414, filed on Feb. 2, 1988, now abandoned.

(51) Int. Cl.$^7$ .......................... G01N 1/02; G01N 33/53; G01N 33/567; C12Q 1/14; C12N 15/63
(52) U.S. Cl. ........................ 435/7.1; 435/7.2; 435/7.21; 435/35; 435/320.1
(58) Field of Search ............................ 435/7.1, 7.2, 35, 435/183, 252.3, 325, 7.21, 320.1; 436/501; 530/350, 399

(56) References Cited

U.S. PATENT DOCUMENTS 5,371,205 A  12/1994  Kelly ........................ 536/23.5

OTHER PUBLICATIONS

Murdoch, C. and Finn, A. (2000) Chemokine receptors and their role in inflammation and infectious diseases. Blood, 95(10): 3032–3042, esp. Table 1.*

Federal Register, 2001, 66(4): 1092–1098.*

Escobedo, "Platelet–Derived Growth Factor Receptors Expressed by cDNA Transfection Couple to a Diverse Group of Cellular Responses Associated with Cell Proliferation" *J. Bio.. Chem.* 263(3): 1482–1487 (1988).

Haynes et al, "Constitutive, Long–Term Production of Human Interferons by Hamster Cells Containing Multiple Copies of a Cloned Interferon Gene" *Nucl. Acid. Res* 11(3):687–706 (1983).

Peralta et al., "Primary Structure and Biochemical Properties of an M2 Muscarinic Receptor" *Science* 236:600–605 (1987).

Gronwald et al., "Cloning and Expression of a cDNA coding for the Human Platelet–Derived Growth Factor Receptor: Evidence for More Than One Receptor Class" *Proc. Natl. Acad. Sci.* 85 3435–3439 (1988).

Matsui et al., "Isolation of a Novel Receptor cDNA Establishes the Existence of Two PDGF Receptor Genes" *Science* 243:800–804 (1989).

* cited by examiner

*Primary Examiner*—Elizabeth Kemmerer
*Assistant Examiner*—Sandra Wegert
(74) *Attorney, Agent, or Firm*—Burns, Doane, Swecker & Mathis, L.L.P.

(57) ABSTRACT

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

12 Claims, 10 Drawing Sheets

FIGURE 1A

```
Asn Phe Glu Trp Thr Tyr Pro Arg Lys Glu Ser Gly Arg Leu Val Glu Pro Val Thr Asp Phe Leu Leu Asp Met Pro Tyr His Ile Arg
AAC TTC GAG TGG ACA TAC CCC CGC AAA GAA AGT GGG CGG CTG GTG GAG CCG GTG ACT GAC TTC CTC TTG GAT ATG CCT TAC CAC ATC CGC
                    220                 230                 240

Ser Ile Leu His Ile Pro Ser Ala Glu Leu Glu Asp Ser Gly Thr Tyr Thr Cys Asn Val Thr Glu Ser Val Asn Asp His Gln Asp Glu
TCC ATC CTG CAC ATC CCC AGT GCC GAG TTA GAA GAC TCG GGG ACC TAC ACC TGC AAT GTG ACG GAG AGT GTG AAT GAC CAT CAG GAT GAA
        250                 260                 270

Lys Ala Ile Asn Ile Thr Val Val Glu Val Ser Gly Tyr Val Arg Leu Leu Gly Thr Leu Gln Phe Ala Glu Leu His Arg Ser
AAG GCC ATC AAC ATC ACC GTG GTT GAG GTG TAC GGC AGC CGG GTG CTC CTG GGA GTG ACA CTA CAA TTT GCT GAG CTG CAT CGG AGC
            280                 290                 300

Arg Thr Leu Gln Val Val Phe Glu Ala Tyr Pro Pro Pro Thr Val Leu Trp Phe Lys Asp Asn Arg Thr Leu Gly Asp Ser Ser Ala Gly
CGG ACA CTG CAG GTA GTG TTC GAG GCC TAC CCA CCG CCC ACT GTC CTG TGG TTC AAA GAC AAC CGC ACC CTG GGC GAC TCC AGC GCT GGC
                    310                 320                 330

Glu Ile Ala Leu Ser Thr Arg Asn Val Ser Glu Thr Arg Tyr Val Ser Glu Leu Thr Leu Val Arg Val Lys Val Ala Glu Ala Arg His
GAA ATC GCC CTG TCC ACG CGC AAC GTG TCA GAG ACC CGG TAT GTG AGT GAG CTG ACA CTG GTT CGC GTG AAG GTG GCA GAG GCT CGC CAC
        340                 350                 360

Tyr Thr Met Arg Ala Phe His Glu Asp Ala Glu Val Gln Leu Ser Phe Gln Leu Gln Ile Asn Val Pro Val Arg Val Leu Glu Leu Ser
TAC ACC ATG CGG GCC TTC CAT GAG GAT GCT GAG GTC CAG CTC TCC TTC CAG CTA CAG ATC AAT GTC CCT GTC CGA GTG CTG GAG CTA AGT
            370                 380                 390

Glu Ser His Pro Asp Ser Gly Glu Gln Thr Val Arg Cys Arg Gly Arg Gly Met Pro Gln Pro Asn Ile Ile Trp Ser Ala Cys Arg Asp
GAG AGC CAC CCT GAC AGT GGG GAA CAG ACA GTC CGC TGT CGT GGC CGG GGC ATG CCC CAG CCC AAC ATC ATC TGG TCT GCC TGC AGA GAC
                    400                 410                 420

Leu Lys Arg Cys Pro Arg Glu Leu Pro Pro Thr Leu Leu Gly Asn Ser Ser Glu Glu Glu Ser Gln Leu Glu Thr Asn Val Thr Tyr Trp
CTC AAA AGG TGT CCA CGT GAG CTG CCG CCC ACG CTG CTG GGG AAC AGT AGT GAG GAG GAG TCC CAG CTG GAG ACC GTG ACT AAC GTG ACG TAC TGG
        430                 440                 450

Glu Glu Gln Glu Phe Glu Val Val Ser Thr Leu Arg Leu Gln His Val Asp Arg Pro Leu Ser Val Arg Cys Thr Leu Arg Asn Ala Ala
GAG GAG CAG GAG TTT GAG GTG GTG AGC ACA CTG CGT CTG CAG CAC GTG GAT CGG CCA CTG TCG GTG CGC TGC ACG CTG CGC AAC GCT
            460                 470                 480

Val Gly Gln Asp Thr Gln Glu Val Ile Val Val Pro His Ser Leu Pro Phe Lys Val Val Val Ile Ser Ala Ile Leu Ala Leu Val Val
GTG GGC CAG GAC ACG CAG GAG GTC ATC GTG GTG CCA CAC TCC CTT CCC TTT AAG GTG GTG GTG ATC TCA GCC ATC CTG GCC CTG GTG GTG
                    490                 500                 510
```

FIGURE 1B

```
Leu Thr Ile Ile Ser Leu Ile Ile Met Leu Trp Gln Lys Lys Pro Arg Tyr Glu Ile Arg Trp Lys Val Ile Glu Ser Val Ser
CTC ACC ATC ATC TCC CTT ATC ATC ATG CTT TGG CAG AAG AAG CCA CGT TAC GAG ATC CGA TGG AAG GTG ATT GAG TCT GTG AGC
                520                      530                      540

Ser Asp Gly His Glu Tyr Ile Tyr Val Asp Pro Met Gln Leu Pro Tyr Asp Ser Thr Trp Glu Leu Pro Arg Asp Gln Leu Val Leu Gly
TCT GAC GGC CAT GAG TAC ATC TAC GTG GAC CCC ATG CAG CTG CCC TAT GAC TCC ACG TGG GAG CTG CCG CGG GAC CAG CTT GTG CTG GGA
            550                      560                      570

Arg Thr Leu Gly Ser Gly Ala Phe Gly Gln Val Val Glu Ala Thr Ala His Gly Leu Ser His Ser Gln Ala Thr Met Lys Val Ala Val
CGC ACC CTC GGC TCT GGG GCC TTT GGG CAG GTG GTG GAG GCC ACG GCT CAT GGC CTG AGC CAT TCT CAG GCC ATG AAA GTG GCC GTC
            580                      590                      600

Lys Met Leu Lys Ser Thr Ala Arg Ser Ser Glu Lys Gln Ala Leu Met Ser Glu Leu Lys Ile Met Ser His Leu Gly Pro His Leu Asn
AAG ATG CTT AAA TCC ACA GCC CGC AGC AGT GAG AAG CAA GCC CTT ATG TCG GAG CTG AAG ATC ATG AGT CAC CTT GGG CCC CAC CTG AAC
            610                      620                      630

Val Val Asn Leu Leu Gly Ala Cys Thr Lys Gly Gly Pro Ile Tyr Ile Ile Thr Glu Tyr Cys Arg Tyr Gly Asp Leu Val Asp Tyr Leu
GTG GTC AAC CTG TTG GGG GCC TGC ACC AAA GGA GGA CCC ATC TAT ATC ATC ACT GAG TAC TGC CGC TAC GGA GAC CTG GTG GAC TAC CTG
            640                      650                      660

His Arg Asn Lys His Thr Phe Leu Gln His His Ser Asp Lys Arg Arg Pro Pro Ser Ala Glu Leu Tyr Ser Asn Ala Leu Pro Val Gly
CAC CGC AAC AAA CAC ACC TTC CTG CAG CAC CAC AGC GAC AAG CGC AAG CCG CCC AGC GCG GAG CTC TAC AGC AAT GCT CTG CCC GTT GGG
            670                      680                      690

Val Pro Leu Pro Ser His Val Ser Leu Thr Gly Glu Ser Asp Gly Gly Tyr Met Asp Met Ser Lys Asp Glu Ser Val Asp Tyr Val Pro
GTC CCC CTG CCC AGC CAT GTG TCC TTG ACC GGG GAG AGC GAC GGT GGC TAC ATG GAC ATG AGC AAG GAC GAG TCG GTG GAC TAT GTG CCC
            700                      710                      720

Met Leu Asp Met Lys Gly Asp Val Lys Tyr Ala Asp Ile Glu Ser Ser Asn Tyr Met Ala Pro Tyr Asp Asn Tyr Val Pro Ser Ala Pro
ATG CTG GAC ATG AAA GGA GAC GTC AAA TAT GCA GAC ATC GAG TCC TCC AAC TAC ATG GCG CCT TAC GAT AAC TAC GTT CCC TCT GCC CCT
            730                      740                      750

Glu Arg Thr Cys Arg Ala Thr Leu Ile Asn Glu Ser Pro Val Leu Ser Tyr Met Asp Leu Val Gly Phe Ser Tyr Gln Val Ala Asn Gly
GAG AGG ACC TGC CGA GCA ACT TTG ATC AAC GAG TCT CCA GTG CTA AGC TAC ATG GAC CTC GTG GGC TTC AGC TAC CAG GTG GCC AAT GGC
            760                      770                      780
```

FIGURE 1C

```
Met Glu Phe Leu Ala Ser Lys Asn Cys Val His Arg Asp Leu Ala Ala Arg Asn Val Leu Ile Cys Glu Gly Lys Leu Val Lys Ile Cys
ATG GAG TTT CTG GCC TCC AAG AAC TGC GTC CAC AGA GAC CTG GCG GCT AGG AAC GTG CTC ATC TGT GAA GGC AAG CTG GTC AAG ATC TGT
                                    790                              800                              810
Asp Phe Gly Leu Ala Arg Asp Ile Met Arg Ala Ser Asn Tyr Ile Ser Lys Gly Ser Thr Phe Leu Pro Leu Lys Trp Met Ala Pro Glu
GAC TTT GGC CTG GCT CGA GAT ATC ATG CGA GCC TCG AAT TAC ATC TCC AAA GGC AGC ACC TTT TTG CCT TTA AAG TGG ATG GCT CCG GAG
                 820                              830                              840
Ser Ile Phe Asn Ser Leu Tyr Thr Thr Leu Ser Asp Val Trp Ser Phe Gly Ile Leu Leu Trp Glu Ile Phe Thr Leu Gly Gly Thr Pro
AGC ATC TTC AAC AGC CTC TAC ACC ACC CTG AGC GAC GTG TGG TCC TTC GGG ATC CTG CTG TGG GAG ATC TTC ACC TTG GGC ACC CCT
                 850                              860                              870
Tyr Pro Glu Leu Pro Met Asn Glu Gln Phe Tyr Asn Ala Ile Lys Arg Gly Tyr Arg Met Ala Gln Pro Ala His Ala Ser Asp Glu Ile
TAC CCA GAG CTG CCC ATG AAT GAG CAG TTC TAC AAT GCC ATC AAA CGG GGT TAC CGC ATG GCC CAG CCT GCC CAT GCC TCC GAC GAG ATC
                 880                              890                              900
Tyr Glu Ile Met Gln Lys Cys Trp Glu Glu Lys Phe Glu Ile Arg Pro Pro Phe Ser Gln Leu Val Leu Leu Leu Glu Arg Leu Leu Gly
TAT GAG ATC ATG CAG AAG TGC TGG GAA GAG AAG TTT GAG ATT CGG CCC CCC TTC TCC CAG CTG GTG CTT CTC CTG GAG AGA CTG TTG GGC
                 910                              920                              930
Glu Gly Tyr Lys Lys Lys Tyr Gln Gln Val Asp Glu Glu Phe Leu Arg Ser Asp His Pro Ala Ile Leu Arg Ser Gln Ala Arg Leu Pro
GAA GGT TAC AAA AAG AAG TAC CAG CAG GTT GAT GAG GAG TTT CTG AGG AGT GAC CAC CCA GCC ATC CTT CGG TCC CAG GCC CGC TTG CCT
                 940                              950                              960
Gly Phe His Gly Leu Arg Ser Pro Leu Asp Thr Ser Ser Val Leu Tyr Thr Ala Val Gln Pro Asn Glu Gly Asp Asn Asp Tyr Ile Ile
GGG TTC CAT GGC CTC CGA TCT CCC CTG GAC ACC AGC AGC GTC CTC TAT ACT GCC GTG CAG CCC AAT GAG GGT GAC AAC GAC TAT ATC ATC
                 970                              980                              990                              1020
Pro Leu Pro Asp Pro Lys Pro Glu Val Ala Asp Glu Gly Pro Leu Glu Gly Ser Pro Ser Leu Ala Ser Ser Thr Leu Asn Glu Val Asn
CCC CTG CCT GAC CCC AAA CCC GAG GTT GCT GAC GAG GGC CCA CTG GAG GGT TCC CCC AGC CTA GCC AGC AGC ACC CTG AAT GAA GTC AAC
                 1000                             1010
Thr Ser Thr Ile Ser Cys Asp Ser Pro Leu Glu Pro Gln Asp Glu Pro Glu Pro Glu Pro Gln Leu Glu Leu Gln Val Glu Pro Glu Pro Glu
ACC TCC ACC ATC TCA TGT GAC AGC CCC CTG GAG CCC CAG GAC GAA CCA GAG CCG GAG CCG CAG CTC GAG CTG CAG GTG GAG CCG GAG
                 1030                             1040                             1050
```

FIGURE 1D 1060                                    1070                                        1074
Pro Glu Leu Glu Gln Leu Pro Asp Ser Gly Cys Pro Ala Pro Arg Ala Glu Ala Glu Asp Ser Phe Leu AM
CCA GAG CTG GAA CAG TTG CCG GAT TCG GGG TGC CCT GCG GCT GAA GCA GAG GAT AGC TTC CTG TAG GGGGCTGGCCCCTACCCTGCCCTG

CCTGAAGCTCCCCCCTGCCAGCACCCAGCATCTCTGCTGGCCTGACCGGGCTTCCTGTCAGCCAGGCTGCCTGTCCCCTTCTGGAAGCTTTCTGCTCCTGACGTGTT
GTGCCCAAACCCTGGGGCTGGCTGGCTTAGGAGGCAAGAAAACTGCAGGGGCCGTGACCAGCCAACTGACTCTGAGCTCTGAGCCAGGGTTCCCCAGGAACTCAGTTT
CCCATATGTAAAATGGGAAAGTTAGGCTTGATGACCCAGAATCTAGGATTCTCTCTCCTGACTTTATCCAGGTGGGAGAGACCCTAGGAGAAGATTCTTGGAGTTACTGAGGTGGTA
AATTAACTTTTTTCTGTTGTCAGCCAGTGCCTCATCCAGAGAAGCAGTCTCCTCCCAGAATCATAGCTCTCCCTATGATGGCCAGTCCAGTCACCATGATGGCCCCCAGCTGGGGCTGTGGGCAGCCTAATTAATGCTGG
CCTAGCCTTGAGCAGTGTAGACAGGACACCCCCAGCCTGCCTCATCCAGAGAAGCAGTCCAGCCCTGCTAGAAGGCAGACGGGCCCCGACTTGGAGCACTTGGAGTGTGGTCCCTGTCCCTGTCAGTGTGGTCCTGGGCACTTGGAGTGTGCCACGTGTGTGCCAGTATATG
CTTTTATCACCCTCAGTCTTGCATCTAATCACCCAGAGTCTCACCAGAGGCTTTGCACATTGGAGGAATCCCTCACCCTCTGGAGCTTTGCACATTAGTCGACTTATTAACTCGATGCTTGCAG
GCCCTGGCTCTGCATCTAGAGTATTCAGGTGGTTGCACATTGTCCCCTTCCCAGGATATCACACATCTCAGGATGAACCATAGAACAGTCAAGACAAGCCATATAAGCTGGGGTCAGCTGGCTCTGGAGATTCAGATCACACATC
ACACTCTGGGGGACTCAGGAAGACCACGGAGTCTGCGTGAAGACATGCCCCCTCTTTCACTACAGGCTTACTAGATGACAGCCGGTGTCCTGGAAAGCCCCAGCAGTG
CACCTGTGCCGAGTCTGCCTCACCAGCTGCCTGTCGAAGACAGAATGAGGACAGTTATGTCTGAAAAGACAAGAAGCCTCAGAGACCTAGCAGTGACATCTCATTGTCCCCAGCACCCTGAAAGGATGTGAAGGATGGGCGCTTTGA
GGTTTGCCCCTCGAGTCTGCCTCACCAGCTGCCCCATCCTGAGGCAGCGCTCCATGGAGGGTTGTAGCCAAGAAGACCCCTAGCAGAAGCTCCACCCTCCTGCACCACCCTGACATTCATTGTCCCCAGCCAGTTGCAGTTGCACCTTACTTCCT
GGGATCCCCAGAGTTGGTCAAGGAGTCAAGGAGGGGTTCTCAATACGGTTCTCAATATGCGTTCTTTTTTTAAGGGAAAGATTTTAATATAATTGATATAATAAACCTGTCTTCTCAAAAAAAAAAAAAAAAAAAAAA
ATGCTATTTGTGATGCTGTTAAGTTTTCTATCTGTTAAGTTTTTCTATCTGTACTTTTTTTAAGGGAAAGATTTTAATATTAAACCTGTCTTCTCAAAAAAAAAAAAAAAAAAAAAA

FIGURE 1E

| | | |
|---|---|---|
| 1 | AAA TGA AAA GGT TGT GCA GCT GAA TTC ATC CTT TTC TCT GAG<br>Asn Glu Lys Val Val Gln Leu Asn Ser Ser Phe Ser Leu Arg | 42 |
| 43 | ATG CTT TGG GGA GAG TGA AGT GAG CTG GCA GTA CCC CAT GTC<br>Cys Phe Gly Glu Ser Glu Val Ser Trp Gln Tyr Pro Met Ser | 84 |
| 85 | TGA AGA AGA GAG CTC CGA TGT GGA AAT CAG AAA TGA AGA AAA<br>Glu Glu Glu Ser Ser Asp Val Glu Ile Arg Asn Glu Glu Asn | 126 |
| 127 | CAA CAG CGG CCT TTC TGT GAC GGT CTT GGA AGT GAG CAG TGC<br>Asn Ser Gly Leu Ser Val Thr Val Leu Glu Val Ser Ser Ala | 168 |
| 169 | CTC GGC GGC CCA CAC AGG GTT GTA CAC TTG CTA TTA CAA CCA<br>Tyr Thr Cys Tyr Tyr Asn His Thr Gln Thr Glu Glu Asn Glu | 210 |
| 211 | CAC TCA GAC AGA AGA GAA TGA GCT TGA AGG CAG GCA CAT TTA<br>Leu Glu Ser Ala Ala His Thr Gly Leu Gly Arg His Ile Tyr | 252 |
| 253 | CAT CTA TGT GCC AGA CCC AGA TGT AGC CTT TGT ACC TCT AGG<br>Ile Tyr Val Pro Asp Pro Asp Val Ala Phe Val Pro Leu Gly | 294 |
| 295 | AAT GAC GGA TTA TTT AGT CAT CGT GGA GGA TGA TGA TTC TGC<br>Met Thr Asp Tyr Leu Val Ile Val Glu Asp Asp Asp Ser Ala | 336 |
| 337 | CAT TAT ACC TTG TCG CAC AAC TGA TCC CGA GAC TCC TGT AAC<br>Ile Ile Pro Cys Arg Thr Thr Asp Pro Glu Thr Pro Val Thr | 378 |
| 379 | CTT ACA CAA CAG TGA GGG GGT GGT ACC TGC CTC CTA CGA CAG<br>Leu His Asn Ser Glu Gly Val Val Pro Ala Ser Tyr Asp Ser | 420 |
| 421 | CAG ACA GGG CTT TAA TGG ACC TTC ACT GTA GGG CCC TAT<br>Arg Gln Gly Phe Asn Gly Thr Phe Thr Val Gly Pro Tyr Ile | 462 |
| 463 | CTG TGA GGC CAC CGT CAA AGG AAA GAA GTT CCA GAC CAT CCC<br>Cys Glu Ala Thr Val Lys Gly Lys Lys Phe Gln Thr Ile Pro | 504 |
| 505 | ATT TAA TGT TTA TGC TTT AAA AGC AAC ATC AGA GCT GGA TCT<br>Phe Asn Val Tyr Ala Leu Lys Ala Thr Ser Glu Leu Asp Leu | 546 |
| 547 | AGA AAT GGA AGC TCT TAA AAC CGT GTA TAA GTC AGG GGA AAC<br>Glu Met Glu Ala Leu Lys Thr Val Tyr Lys Ser Gly Glu Thr | 588 |
| 589 | GAT TGT GGT CAC CTG TGC TGT TTT TAA CAA TGA GGT GGT TGA<br>Ile Val Val Thr Cys Ala Val Phe Asn Asn Glu Val Val Asp | 630 |
| 631 | CCT TCA ATG GAC TTA CCC TGG AGA AGT GAA AGG CAA AGG CAT<br>Leu Gln Trp Thr Tyr Pro Gly Glu Val Lys Gly Lys Gly Ile | 672 |

FIGURE 2A

673  CAC AAT GCT GGA AGA AAT CAA AGT CCC ATC CAT CAA ATT GGT  714
     Thr Met Leu Glu Glu Ile Lys Val Pro Ser Ile Lys Leu Val

715  GTA CAC TTT GAC GGT CCC CGA GGC CAC GGT GAA AGA CAG TGG  756
     Tyr Thr Leu Thr Val Pro Glu Ala Thr Val Lys Asp Ser Gly

757  AGA TTA CGA ATG TGC TGC CCG CCA GGC TAC CAG GGA GGT CAA  798
     Asp Tyr Glu Cys Ala Ala Arg Gln Ala Thr Arg Glu Val Lys

799  AGA AAT GAA GAA AGT CAC TAT TTC TGT CCA TGA GAA AGG TTT  840
     Glu Met Lys Lys Val Thr Ile Ser Val His Glu Lys Gly Phe

841  CAT TGA AAT CAA ACC CAC CTT CAG CCA GTT GGA AGC TGT CAA  882
     Ile Glu Ile Lys Pro Thr Phe Ser Gln Leu Glu Ala Val Asn

883  CCT GCA TGA AGT CAA ACA TTT TGT TGT AGA GGT GCG GGC CTA  924
     Leu His Glu Val Lys His Phe Val Val Glu Val Arg Ala Tyr

925  CCC ACC TCC CAG GAT ATC CTG GCT GAA AAA CAA TCT GAC TCT  966
     Pro Pro Pro Arg Ile Ser Trp Leu Lys Asn Asn Leu Thr Leu

967  GAT TGA AAA TCT CAC TGA GAT CAC CAC TGA TGT GGA AAA GAT  1008
     Ile Glu Asn Leu Thr Glu Ile Thr Thr Asp Val Glu Lys Ile

1009 TCA GGA AAT AAG GTA TCG AAG CAA ATT AAA GCT GAT CCG TGC  1050
     Gln Glu Ile Arg Tyr Arg Ser Lys Leu Lys Leu Ile Arg Ala

1051 TAA CCA AGA AGA CAG TGG CCA TTA TAC TAT TGT AGC TCA AAA  1092
     Asn Gln Glu Asp Ser Gly His Tyr Thr Ile Val Ala Gln Asn

1093 TGA AGA TGC TGT GAA GAG CTA TAC TTT TGA ACT GTT AAC TCA  1134
     Glu Asp Ala Val Lys Ser Tyr Thr Phe Glu Leu Leu Thr Gln

1135 AGT TCC TTC ATC CAT TCT GGA CTT GGT CGA TGA TCA CCA TGG  1176
     Val Pro Ser Ser Ile Leu Asp Leu Val Asp Asp His His Gly

1177 CTC AAC TGG GGG ACA GAC GGT GAG GTG CAC AGC TGA AGG CAC  1218
     Ser Thr Gly Gly Gln Thr Val Arg Cys Thr Ala Glu Gly Thr

1219 GCC GCT TCC TGA TAT TGA GTG GAT GAT ATG CAA AGA TAT TAA  1260
     Pro Leu Pro Asp Ile Glu Trp Met Ile  Cys Lys Asp Ile Lys

1261 GAA ATG TAA TAA TGA AAC TTC CTG GAC TAT TTT GGC AAC AA  1302
     Lys Cys Asn Asn Glu Thr Ser Trp Thr Ile Leu Ala Asn Asn

1303 TGT CTC AAA CAT CAT CAC GGA GAT CCA CTC CCG AGA CAG GAG  1344
     Val Ser Asn Ile Ile Thr Glu Ile His Ser Arg Asp Arg Ser

FIGURE 2B

```
1345 TAC CGT GGA GGG CCG TGT GAC TTT CGC CAA AGT GGA GGA GAC    1386
     Thr Val Glu Gly Arg Val Thr Phe Ala Lys Val Glu Glu Thr

1387 CAT CGC CGT GCG ATG CCT GGC TAA GAA TCT CCT TGG AGC TGA    1428
     Ile Ala Val Arg Cys Leu Ala Lys Asn Leu Leu Gly Ala Glu

1429 GAA CCG AGA GCT GAA GCT GGT GGC TCC ACC CCT GCG TTC TGA    1470
     Asn Arg Glu Leu Lys Leu Val Ala Pro Thr Leu Arg Ser Glu

1471 ACT CAC GGT GGC TGC TGC AGT CCT GGT GCT GTT GGT GAT TGT    1512
     Leu Thr Val Ala Ala Ala Val Leu Val Leu Leu Val Ile Val

1513 GAT CAT CTC ACT TAT TGT CCT GGT TGT CAT TTG AAA CAA GAA    1554
     Ile Ile Ser Leu Ile Val Leu Val Val Ile Trp Lys Gln Lys

1555 ACC GAG GTA TGA AAT TCG CTG GAG GGT CAT TGA ATC AAT CAG    1596
     Pro Arg Tyr Glu Ile Arg Trp Arg Val Ile Glu Ser Ile Ser

1597 CCC GGA TGG ACA TGA ATA TAT TTA TGT GGA CCC GAT GCA GCT    1638
     Pro Asp Gly His Glu Tyr Ile Tyr Val Asp Pro Met Gln Leu

1639 GCC TTA TGA CTC AAG ATG GGA GTT CCA AGA TGG ACT AGT    1680
     Pro Tyr Asp Ser Arg Trp Glu Phe Pro Arg Asp Gly Leu Val

1681 GCT TGG TCG GGT CTT GGG GTC TGG AGC GTT TGG AAG GTG GT    1722
     Leu Gly Arg Val Leu Gly Ser Gly Ala Phe Gly Lys Val Val

1723 TGA AGG AAC AGC CTA TGG ATT AAG CCG GTC CCA ACC TGT CAT    1764
     Glu Gly Thr Ala Tyr Gly Leu Ser Arg Ser Gln Pro Val Met

1765 GAA AGT TGC AGT GAA CAT GCT AAA ACC CAC GGC CAG ATC CAG    1806
     Lys Val Ala Val Asn Met Leu Lys Pro Thr Ala Arg Ser Ser

1807 TGA AAA ACA AGC TCT CAT GTC TGA ACT GAA GAT AAT GAC TCA    1848
     Glu Lys Gln Ala Leu Met Ser Glu Leu Lys Ile Met Thr His

1849 CCT GGG GCC ACA TTT GAA CAT TGT AAA CTT GCT GGG AGC CTG    1890
     Leu Gly Pro His Leu Asn Ile Val Asn Leu Leu Gly Ala Cys

1891 CAC CAA GTC AGG CCC CAT TTA CAT CAT CAC AGA GTA TTG CTT    1932
     Thr Lys Ser Gly Pro Ile Tyr Ile Ile Thr Glu Tyr Cys Phe

1933 CTA TGG AGA TTT GGT CAA CTA TTT GCA TAA GAA TAG GGA TAG    1974
     Arg Asp Ser Phe Leu Ser His His Pro Glu Lys Pro Lys Lys

1975 CTT CCT GAG CCA CCA CCC AGA GAA GCC AAA GAA AGA GCT GGA    2016
     Glu Leu Tyr Gly Asp Leu Val Asn Tyr Leu His Lys Asn Asp
```

FIGURE 2C

```
2017 TAT CTT TGG ATT GAA CCC TGC TGA TGA AAG CAC ACG GAG CTA    2058
     Ile Phe Gly Leu Asn Pro Ala Asp Glu Ser Thr Arg Ser Tyr

2059 TGT TAT TTT ATC TTT TGA AAA CAA TGG TGA CTA CAT GGA CAT    2100
     Val Ile Leu Ser Phe Glu Asn Asn Gly Asp Tyr Met Asp Met

2101 GAA GCA GGC TGA TAC TAC ACA GTA TGT CCC CAT GCT AGA AAG    2142
     Lys Gln Ala Asp Thr Thr Gln Tyr Val Pro Met Leu Glu Arg

2143 GAA AGA GGT TTC TAA ATA TTC CGA CGT CCA GAG ATC ACT CTA    2184
     Lys Glu Val Ser Lys Tyr Ser Asp Val Gln Arg Ser Leu Tyr

2185 TGA TCG TCC AGC CTC ATA TAA GAA GAA ATC TAT GTT AGA CTC    2226
     Asp Arg Pro Ala Ser Tyr Lys Lys Lys Ser Met Leu Asp Ser

2227 AGA AGT CAA AAA CCT CCT TTC AGA TGA TAA CTC AGA AGG CCT    2268
     Glu Val Lys Asn Leu Leu Ser Asp Asp Asn Ser Glu Gly Leu

2269 TAC TTT ATT GGA TTT GTT GAG CTT CAC CTA TCA AGT TGC CCG    2310
     Thr Leu Leu Asp Leu Leu Ser Phe Thr Tyr Gln Val Ala Arg

2311 AGG AAT GGA GTT TTT GGC TTC AAA AAA TTG TGT CCA CCG TGA    2352
     Gly Met Glu Phe Leu Ala Ser Lys Asn Cys Val His Arg Asp

2353 TCT GGC TGC TCG CAA CGT CCT CCT GGC ACA GGG AAA AAT TGT    2394
     Leu Ala Ala Arg Asn Val Leu Leu Ala Gln Gly Lys Ile Val

2395 GAA GAT CTG TGA CTT TGG CCT GGC CAG AGA CAT CAT GCA TGA    2436
     Lys Ile Cys Asp Phe Gly Leu Ala Arg Asp Ile Met His Asp

2437 TTC GTT CTA TGT GTC GAA AGG CAG TAC CTT TCT GCC CGT GAA    2478
     Ser Phe Tyr Val Ser Lys Gly Ser Thr Phe Leu Pro Val Lys

2479 GTG GAT GGC TCC TGA GAG CAT CTT TGA CAA CCT CTA CAC CAC    2520
     Trp Met Ala Pro Glu Ser Ile Phe Asp Asn Leu Tyr Thr Thr

2521 ACT GAG TGA TGT CTG GTC TTA TGG CAT TCT GCT CTG GGA GAT    2562
     Leu Ser Asp Val Trp Ser Tyr Gly Ile Leu Leu Trp Glu Ile

2563 CTT TTC CCT TGG TGG CAC CCC TTA CCC CGG CAT GAT GGT GGA    2604
     Phe Ser Leu Gly Gly Thr Pro Tyr Pro Gly Met Met Val Asp

2605 TTC TAC TTT CTA CAA TAA GAT CAA GAG TGG GTA CCG GAT GGC    2646
     Ser Thr Phe Tyr Asn Lys Ile Lys Ser Gly Tyr Arg Met Ala

2647 CAA GCC TGA CCA CGC TAC CAG TGA AGT CTA CGA GAT CAT GGT    2688
     Lys Pro Asp His Ala Thr Ser Glu Val Tyr Glu Ile Met Val
```

FIGURE 2D

```
2689 GAA ATG CTG GAA CAG TGA GCC GGA GAA GAG ACC CTC CTT TTA    2730
      Lys Cys Trp Asn Ser Glu Pro Glu Lys Arg Pro Ser Phe Tyr

2731 CCA CCT GAG TGA GAT TGT GGA GAA TCT GCT GCC TGG ACA ATA    2772
      His Leu Ser Glu Ile Val Glu Asn Leu Leu Pro Gly Gln Tyr
2773 TAA AAA GAG TTA TGA AAA AAT TCA CCT GGA CTT CCT GAA GAG    2814
      Lys Lys Ser Tyr Glu Lys Ile His Leu Asp Phe Leu Lys Ser

2815 TGA CCA TCC TGC TGT GGC ACG CAT GCG TGT GGA CTC AGA CAA    2856
      Asp His Pro Ala Val Ala Arg Met Arg Val Asp Ser Asp Asn

2857 TGC ATA CAT TGG TGT CAC CTA CAA AAA CGA GGA AGA CAA GCT    2898
      Ala Tyr Ile Gly Val Thr Tyr Lys Asn Glu Glu Asp Lys Leu

2899 GAA GGA CTG GGA GGG TGG TCT GGA TGA GCA GAG ACT GAG CGC    2940
      Lys Asp Trp Glu Gly Gly Leu Asp Glu Gln Arg Leu Ser Ala

2941 TGA CAG TGG CTA CAT CAT TCC TCT GCC TGA CAT TGA CCC TGT    2982
      Asp Ser Gly Tyr Ile Ile Pro Leu Pro Asp Ile Asp Pro Val

2983 CCC TGA GGA GGA GGA CCT GGG CAA GAG GAA CAG ACA CAG CTC    3024
      Pro Glu Glu Glu Asp Leu Gly Lys Arg Asn Arg His Ser Ser

3025 GCA GAC CTC TGA AGA GAG TGC CAT TGA GAC GGG TTC CAG CAG    3066
      Gln Thr Ser Glu Glu Ser Ala Ile Glu Thr Gly Ser Ser Ser

3067 TTC CAC CTT CAT CAA GAG AGA GGA CGA GAC CAT TGA AGA CAT    3108
      Ser Thr Phe Ile Lys Arg Glu Asp Glu Thr Ile Glu Asp Ile

3109 CGA CAT GAT GGA CGA CAT CGG CAT AGA CTC TTC AGA CCT GGT    3150
      Asp Met Met Asp Asp Ile Gly Ile Asp Ser Ser Asp Leu Val

3151 GGA AGA CAG CTT CCT GTA ACT GGC GGA TTC GAG GGT TCC TTC    3192
      Glu Asp Ser Phe Leu  *  Leu Ala Asp Ser Arg Val Pro Ser

3193 CAC TTC T      3199
      Thr Ser
```

FIGURE 2E 

METHODS FOR DETECTING HUMAN PLATELET-DERIVED GROWTH FACTOR RECEPTOR AGONISTS AND ANTAGONISTS

CROSS REFERENCE TO RELATED APPLICATION

This application is a divisional of application Ser. No. 08/240,294, filed May 9, 1994, U.S. Pat. No. 6,110,737, which is a continuation of application Ser. No. 08/031,082, filed Mar. 15, 1993, now abandoned, which is a continuation of application Ser. No. 07/771,829, filed Oct. 7, 1991, now abandoned, which is a continuation of application Ser. No. 07/309,322, filed Feb. 10, 1989, now abandoned, which is a continuation in part of application Ser. No. 07/151,414, filed Feb. 2, 1988, now abandoned.

INTRODUCTION

TECHNICAL FIELD

The present invention relates to growth factors and their receptors and, in particular, to human platelet-derived growth factor receptor.

BACKGROUND OF THE INVENTION

Platelet-derived growth factor (PDGF) is a major mitogen for cells of mesenchymal origin. The protein is a 32 kDa protein heterodimer composed of two polypeptide chains, A and B, linked by disulfide bonds. In addition to the PDGF AB heterodimer, two homodimeric forms of PDGF, denoted AA and BB, have been identified.

Until recently, whether the AA isoform bound to a receptor was not known. Now, a single receptor has been identified which has been shown to bind all three isoforms of hPDGF. However, the reported affinities of hPDGF receptors of different cell types for different isoforms of hPDGF has lead to speculation that there are more than one type of hPDGF receptor.

The first event in PDGF-mediated mitogenesis is the binding of PDGF to its receptor at the cell membrane. This interaction triggers a diverse group of early cellular responses including activation of receptor tyrosine kinase, increased phosphatidylinositol turnover, enhanced expression of a group of genes, activation of phospholipase A2, changes in cell shape, increase in cellular calcium concentration, changes in intracellular pH, and internalization and degradation of bound PDGF. These changes are followed by an increase in the rate of proliferation of the target cells.

While the ability of a polypeptide to stimulate growth of a particular cell type in vitro does not prove that it serves the same function in vivo, the role of many growth factors on cells is being studied to attempt to determine the role that the factors play in the whole organism. In vitro, platelet-derived growth factor is a major polypeptide mitogen in serum for cells of mesenchymal origin such as fibroblasts, smooth muscle cells and glial cells. In vivo, PDGF circulates stored in the $\alpha$ granules of blood platelets and does not circulate freely in blood. During blood clotting and platelet adhesion, the granules are released, often at sites of injured blood vessels, implicating PDGF in the repair of blood vessels. PDGF also stimulates migration of arterial smooth muscle cells from the medial to the intimal layer of the artery where they then proliferate as an early response to injury.

PDGF is being studied to determine how cell proliferation is controlled in the body. The growth factor has been implicated in wound healing, in atherosclerosis, and in stimulating genes associated with cancerous transformation of cells, particularly c-myc and c-fos. Therefore, PDGF agonists may be useful in promoting wound healing. PDGF antagonists may be useful in preventing atherosclerosis, in retarding blood vessel narrowing that occurs after cardiovascular intervention and in controlling cancerous proliferation.

Relevant Literature

The mouse PDGF receptor has been identified, purified (Daniel et al., *Proc. Natl. Acad. Sci USA* (1985) 82:2684–2687), and sequenced (Yarden et al., *Nature* (1986) 323:226–232). A cDNA sequence encoding a human PDGF receptor was identified, sequenced and used to transfect cells lacking the receptor (Escobedo et al., *Science* (1988) 240:1532–1538; Claesson-Welsh et al., *Mol. Cell. Biol.* (1988) 8:3476–3486). Studies using the transfected cells gave differing results, demonstrating that the receptor binds specifically to all three isoforms of hPDGF, preferentially binding the BB homodimer (Escobedo et al., supra.) and that the receptor binds the BB and AB isoforms but not the AA isoform, at least at the concentration tested (Claesson-Welsh et al., supra.). Binding sites on different cell types were reported to have different affinities for different PDGF isoforms (Kazlauskas et al., *EMBO J.* (1988) 7:3727–3735). Two classes of PDGF receptor were reported to recognize different isoforms of PDGF (Hart et al., *Science* (1988) 240:1529–1531).

SUMMARY OF THE INVENTION

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

BRIEF DESCRIPTION OF THE FIGURES

FIGS. 1A–E show the nucleotide sequence (SEQ ID NO: 1) of a cDNA encoding a B-hPDGF-R together with the deduced amino acid sequence of the receptor precursor.

FIGS. 2A–E show the nucleotide sequence (SEQ ID NO: 2) of a cDNA encoding A-hPDGF-R together with the deduced amino acid sequence of the receptor.

DESCRIPTION OF SPECIFIC EMBODIMENTS

Methods for producing human platelet-derived growth factor (hPDGF-R) and nucleic and constructs for such production are provided as well as cells comprising the hPDGF-R where the composition and cells may find use in diagnosis, evaluation of drugs affecting the transduction of the hPDGF-R signal and in the treatment of diseases associated with hPDGF-R. The construct can be used to transfect cells, providing a membrane-bound receptor that is functionally equivalent to the wild-type receptor, and conferring a PDGF-sensitive mitogenic response on cells lacking the receptor. The transfected cells can be used as a model for studying the PDGF-induced response of cells, determining the regions involved in transducing the signal in response to PDGF binding and evaluating drugs for their physiologic activity. The encoded receptor or its binding region also find use in evaluating PDGF agonists. Other utilities for the DNA sequence include use of fragments of the sequence as probes to detect deletions in the region of chromosome 5 where a number of growth-control related genes are clustered, to detect deletions in chromosome 4 near the c-kit oncogene or to detect other genes encoding tyrosine kinase or homologous proteins.

The hPDGF receptor that binds the BB homodimer with high affinity has been variously referred as the B receptor, the β receptor and, as used herein, the type B receptor (B-hPDGF-R). The hPDGF receptor that preferentially binds the AA homodimer is referred to as the A receptor, the α receptor and, as used herein, the type A receptor (A-hPDGF-R).

Figure 1A:
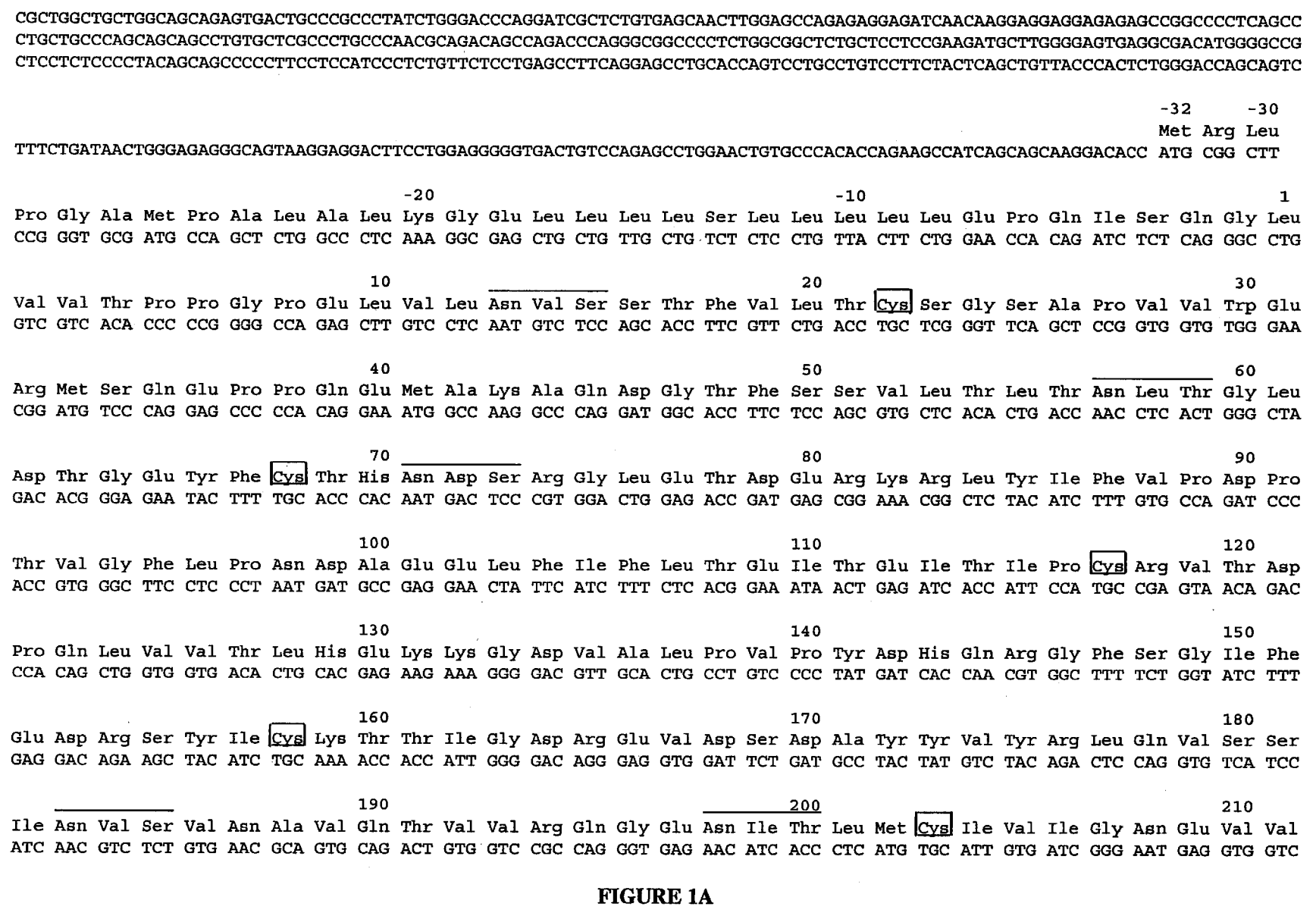

The nucleotide sequence of a cDNA sequence encoding B-hPDGF-R is set forth in FIG. 1 together with the deduced amino acid sequence of the receptor precursor. The sequence beginning at the amino acid numbered 1 corresponds to the amino terminus of human PDGF-R. The first 32 amino acids (designated −32 to −1) encode the signal peptide sequence. The dark bar underlines the transmembrane sequence (amino acid residues 500 to 524). Potential N-glycosylation sites are indicated by a line. The polyadenylation site in the 3' end of the cDNA has been underlined.

The nucleotide sequence of a cDNA sequence encoding A-hPDGF-R is set forth in FIG. 2 together with the deduced amino acid sequence of the receptor. The sequence of the 3' untranslated region and the signal sequence-encoding region are not shown. The reading frame for the amino acid sequence begins at nucleotide 2. The "*" at nucleotides 3167–3169 (TAA) indicates a stop codon for chain termination of the receptor protein sequence. The coding sequence for the extracellular domain is from nucleotide 1 through 1471. The transmembrane region is from 1472 through 1546. The intracellular region is from 1547–3166. The tyrosine kinase region is encoded by residues 1669–1982 and 2279 to about 2700.

As seen in FIGS. 1 and 2, the intracellular, tyrosine kinase domain of the type A and type B receptors have about 80% identical residues. The extracellular domain of the type A and B receptors have about 34–35% identical residues, an additional 14% of the remaining residues being conservative substitutions. The transmembrane regions of the hPDGF receptors have about 48% identical residues. Of the 52% of residues that differ, 70% are conservative substitutions. As seen in the tables, both receptor sequences have a 107 amino acid insertion interrupting the tyrosine kinase region (encoded by residues 1983–2278 of type A).

The DNA compositions of this invention may be derived from genomic DNA or cDNA, prepared by synthesis or combinations thereof. The DNA compositions may include the complete coding region encoding hPDGF-R or fragments thereof of interest, usually comprising at least 8 codons (24 bp), more usually at least 12 codons, where one or more introns may be present. While for the most part the wild-type sequence will be employed, in some situations one or more mutations may be introduced, such as deletions, substitutions or insertions resulting in changes in the amino acid sequence or providing silent mutations. The genomic sequence will usually not exceed 50 kbp, more usually not exceed about 10 kbp, preferably not greater than 6 kbp.

A DNA fragment encoding hPDGF-R finds use to isolate DNA encoding PDGF receptors of other species which share substantial homologies with hPDGF-R. Fragments from the intracellular tyrosine kinase region can be used to isolate other tyrosine kinases. Portions of the DNA fragment having at least about 10 nucleotides, usually at least about 20 nucleotides, and fewer than about 6 knt (kilonucleotides), usually fewer than about 0.5 knt, from a DNA sequence encoding hPDGF-R find use as probes. The probes can be used to determine whether mRNA encoding hPDGF-R is present in a cell.

Additionally, the type B human PDGF receptor gene is located at a site on chromosome 5 where a number of growth control related genes are clustered. At least one genetic disease, 5q minus syndrome, has been shown to involve a deletion in this region. The type A receptor gene is located on chromosome 4 near the c-kit oncogene. Fragments of the hPDGF-R gene sequence may be used as a marker to probe the structure of these important regions of the genome and to diagnose genetic diseases associated with those areas of the genome.

The DNA fragment or portions thereof can also be used to prepare an expression construct for hPDGF-R. The construct comprises one or more DNA sequences encoding hPDGF-R under the transcriptional control of the native or other than the native promoter. When more than one sequence encoding hPDGF-R is present in the construct, the sequences may encode the same or different isoforms of the receptor, usually different. Usually the promoter will be a eukaryotic promoter for expression in a mammalian cell, where the mammalian cell may or may not lack PDGF receptors. In cases where one wishes to expand the DNA sequence or produce the receptor protein or fragments thereof in a prokaryotic host, the promoter may also be a prokaryotic promoter. Usually a strong promoter will be employed to provide for high level transcription and expression.

The expression construct may be part of a vector capable of stable extrachromosomal maintenance in an appropriate cellular host or may be integrated into host genomes. The expression cassette may be bordered by sequences which allow for insertion into a host, such as transposon sequences, lysogenic viral sequences, or the like. Normally, markers are provided with the expression cassette which allow for selection of host cells containing the expression cassette. The marker may be on the same or a different DNA molecule, desirably the same DNA molecule.

In mammalian cells, the receptor gene itself may provide a convenient marker. However, in prokaryotic cells, markers such as resistance to a cytotoxic agent, complementation of an auxotrophic host to prototrophy, production of a detectable product, etc. will be more convenient.

The expression construct can be joined to a replication system recognized by the intended host cell. Various replication systems include viral replication systems such as retroviruses, simian virus, bovine papilloma virus, or the like In addition, the construct may be joined to an amplifiable gene, e.g., DHFR gene, so that multiple copies of the hPDGF-R gene may be made.

Introduction of the construct into the host will vary depending upon the particular construction. Introduction can be achieved by any convenient means, including fusion, conjugation, transfection, transduction, electroporation, injection, or the like, as amply described in the scientific literature. Introduction of constructs encoding different isoforms of the receptor into a single host cell is also contemplated. The host cells will normally be immortalized cells, that is cells that can be continuously passaged in culture. For the most part, these cells may be any convenient mammalian cell line which is able to express hPDGF-R and where desirable, process the polypeptide so as to provide a mature polypeptide. By processing is intended glycosylation, ubiquitination, disulfide bond formation, or the like. Usually the host will be able to recognize the signal sequence for inserting hPDGF-R into the membrane of the cell. If secretion is desired, the transmembrane locator sequence may be deleted or mutated to prevent membrane insertion of the protein.

A wide variety of hosts may be employed for expression of the peptides, both prokaryotic and eukaryotic. Useful hosts include bacteria, such as E. coli, yeast, filamentous fungus, immortalized mammalian cells, such as various mouse lines, monkey lines, Chinese hamster ovary lines, human lines, or the like. For the most part, the mammalian cells will be immortalized cell lines. In some cases, the cells may be isolated from a neoplastic host, or wild-type cells may be transformed with oncogenes, tumor causing viruses, or the like.

Under may circumstances, it will be desirable to transfect mammalian cells which lack a PDGF receptor where the signal sequence directs the peptide into the cell membrane. Lymphocytes and cardiac myocytes are primary cells which lack a receptor. Also, Chinese hamster ovary cells (CHO), epithelial cells lines and a number of human tumor cell lines lack PDGF receptors.

Transfected cells find use as a model for studying cellular responses to PDGF. For controlled investigation, mammalian cells which lack a PDGF receptor can be transfected with an expression construct comprising a DNA sequence encoding hPDGF-R. Cells are produced that encode a receptor that is functionally equivalent to the wild-type receptor and confer a PDGF-sensitive mitogenic response on the cell. In this way, the binding properties of the naturally-occurring PDGF may be analyzed, fragments tested as well as synthetic compounds both proteinaceous and non-proteinaceous. As demonstrated in the Experimental section, transfected cells were used to determine that the AA form of PDGF activates the type B receptor tyrosine kinase. The presence of the type A and type B receptors in a single cell facilitates the study of receptor binding properties.

In addition to studying PDGF-mediated mitogenesis, the transfected cells can be used to evaluate a drug's ability to function as a PDGF agonist or antagonist. In particular, transfected cells can be contacted with the test drug, and the amount of receptor tyrosine kinase activation or the rate of DNA synthesis can be determined in comparison to control cells in the presence or absence of PDGF, or analogs thereof of known activity.

The hPDGF-R protein expressed by transfected cells also finds use. If the peptide is secreted, the peptide may be isolated from the supernatant in which the expression host is grown. If not secreted, the peptide may be isolated from a lysate of the expression host. The peptide may then be isolated by convenient techniques employing HPLC, electrophoresis, gradient centrifugation, affinity chromatography, particularly using PDGF, etc., to provide a substantially pure product, particularly free of cell component contaminants.

The receptor protein or amino acids beginning at about 33 through about 500 of the amino terminal sequence of the receptor which form the external domain, binding portion of the receptor protein find use to affinity purify PDGF. The external domain can also be used affixed to a solid substrate or free in solution to determine drugs useful as PDGF agonists and antagonists.

The protein or the intracellular portion of the protein, beginning at about amino acid 525 through the carboxy terminal amino acid of hPDGF-R, also find use as an enzyme having tyrosine kinase activity. Additionally, amino acids 1 through 32 of the amino terminal sequence of the type B receptor comprise a signal sequence which directs the structural protein through the membrane of a transfected cell. The signal sequence can be used with hPDGF-R, but also finds use with other proteins.

Peptides or portions thereof may also be used for producing antibodies, either polyclonal or monoclonal. Antibodies are produced by immunizing an appropriate vertebrate host, e.g., mouse, with the peptide itself, or in conjunction with a conventional adjuvant. Usually two or more immunizations will be involved, and the blood or spleen will be harvested a few days after the last injection.

For polyclonal antisera, the immunoglobulins may be precipitated, isolated and purified, including affinity purification. For monoclonal antibodies, the splenocytes normally will be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570 and 4,618,577.

The following examples are offered by way of illustration and not by way of limitation.

EXPERIMENTAL

Screening of Human Kidney λGT11 cDNA Library and Human Placenta λGT10 cDNA Library A full-length DNA sequence encoding the mouse PDGF receptor (mPDGF-R) protein was used as a probe to screen 250,000 plaques of a human kidney cDNA library. Nick translation was used to prepare a probe with specific activity of $12 \times 10^8$ cpm per $\mu$g. The filters were incubated with the probe ($10^5$ cpm per ml) in hybridization buffer containing 30% formamide, 1×Denhardt's solution, 5×SC, 0.02M sodium phosphate pH 6.5 and 500 $\mu$g per ml of salmon sperm DNA. After 14 hr. of hybridization at 40° C., the filters were washed four times at 55° C. with 0.2×SSC and 0.1% SDS and two additional times at 65° C. with 0.2×SSC. The filters were then air dried and exposed for 16 hrs.

Ten positive clones were obtained which were rescreened with the full-length mPDGF-R probe. Individual clones were isolated and analyzed by restriction analysis using EcoRI endonuclease. The clone containing the largest insert (2.3 kb), designated clone HK-6, was further characterized and sequenced using dideoxy terminators. Clone HK-6 contained the receptor sequence from nucleotide 3554 to nucleotide 5691 plus nine bases from the poly A tail.

A nick-translated probe, prepared from the 2.3 kb HK-6 DNA, was used to screen 250,000 plaques of a human placenta cDNA library. This screening was performed at high hybridization stringency (50% formamide in the hybridization buffer described above). The filters were incubated with $5 \times 10^5$ cpm per ml of probe for 14–16 hrs. at 42° C. The filters were than washed at 65° C. in 0.1% SSC and 0.1% SDS four times.

After secondary screening with the HK-6 probe, seven clones were selected and analyzed by restriction digestion with EcoRI endonuclease. A clone (HP-7) that contained a 4.5.kb insert was selected and characterized. The sequence of that clone is described in FIG. 1 and encodes the type B human PDGF receptor (B-hPDGF-R).

Construction of Expression Vector

The 4.5 kb DNA fragment containing the complete coding sequence for the type B human PDGF receptor was isolated from the HP-7 clone by EcoRI digestion. The gel purified fragment was cloned into the EcoRI site in the polylinker region of SV40 expression vector PSV7C. The pSV7d expression vector (provided by P. Luciw, University of California, Davis) was a pML derivative containing the SV40 early promoter region (SV40 nucleotides 5190–5270), a synthetic polylinker with restriction sites for EcoRI, SmaI, XbaI, and SalI followed by three translation terminator codons (TAA) and the SV40 polyadenylation signal (SV40 nucleotides 2556–2770) (Truett et al., *DNA* (1984) 4:333–349). The EcoRI fragment containing the cDNA sequence obtained from the HP-7 clone was inserted at the EcoRI site of the pSV7d. In the resulting expression vector, the B-hPDGF -receptor gene was under transcriptional control of the SV40 promoter.

To ensure the proper orientation of the PDGF receptor insert (4.5 kb) with respect to the SV40 promoter, the positive clones were digested with SmaI endonuclease which cuts at position 573 of the receptor sequence and in the polylinker region of the expression vector.

Clones containing the receptor in the proper transcriptional orientation released a 4.0 kb insert in addition to the 3.2 kb fragment containing the expression vector plus 573 base pairs of the 5' end of the receptor. This plasmid, PSVRH5 was used to co-transfect cells with PSV2 neo plasmid that confers resistance to the antibiotic neomycin.

Cell Culture and Transfection of CHO Cells

CHO cell clone KI, obtained from the U.C.S.F. Tissue Culture Facility, were grown in Ham's F-12 media supplemented with 10% FCS (U.C.S.F. Tissue Culture Facility) and penicillin and streptomycin at 37° C. in 5% $CO_2$/95% air.

pSVRH5 plasmid DNA (10 μu) and pSV2 neo (1 μg) were used to co-transfect $1\times10^6$ CHO cells by the calcium precipitation technique (Van der Eb et al., *Methods Enzymology* (1980) 65:826–839), with the addition of 10 μg chloroquinone diphosphate (CDP) to prevent degradation of the transfected DNA (Luthman and Magnusson, *Nucl. Acid Res.* (1983) 11:1295–1308). After 12 hrs. of exposure to the DNA, the cells were trypsinized and replated at 1:5 dilution. Twenty-four hours later, the antibiotic G418 (GIBCO), an analog of neomycin, was added to the cultures at a concentration of 400 μg/ml.

After two weeks under selection, independent colonies were picked and transferred to 24-well plates. Confluent cultures were assayed for the presence of PDGF receptor by immunoblot using anti-receptor antibodies. Colonies that were positive by this assay were single-cell cloned by end-limiting dilution.

Stable transfected clones were tested for the expression of the type B PDGF receptor message measured by RNA protection assays (Zinn et al., *Cell* (1983) 34:865–879) and for the presence of PDGF-stimulated receptor protein detected by antiphosphotyrosine antibodies (Frackelton et al., *J. Biol. Chem.* (1984) 259:7909–7915).

Expression of B-hPDGF-R cDNA in CHO Cells

CHO cells transfected with plasmid DNA containing the human receptor cDNA under the transcriptional control of the SV40 early promoter (CHO-HR5) and CHO cells transfected with a similar plasmid containing the mouse receptor cDNA (CHO-R18) were solubilized as previously described (Escobedo et al., *J. Biol. Chem.* (1988) 263:1482–1487). Extracts were analyzed by Western blot analysis using an antibody that specifically recognizes sequences in the receptor carboxy-terminal region as previously described in (Escobedo et al., supra; Keating et al., ibid. (1987) 262:7932–7937). The 195 kDa protein is the mature receptor and the 160 kDa protein is the receptor precursor.

The expression of the receptor protein in the transfectants was demonstrated by using antibodies that recognize an intracellular sequence in the receptor. The clone that had the highest level of human receptor expression was chosen for further study. This transfectant had receptors that were labeled with $^{125}$I-PDGF as shown by the competitive binding studies described below.

Competitive Binding of the Different Forms of PDGF to the Type B Receptor

The ability of the human recombinant AA and BB homodimers (Collins et al., *Nature* (1987) 328:621–624) to compete for the type B receptor sites and displace $^{125}$I-labeled PDGF was studied. Each homodimer was produced selectively by a yeast expression system (Brake et al., *Proc. Natl. Acad. Sci.* (*USA*) (1984) 81:4642–4646) and was purified from yeast media that is devoid of other mesenchymal cell growth factors, thus avoiding the artifact of contamination by factors that might be present in mammalian expression systems.

BALB/c 3T3 cells and CHO transfectants (CHO-HR5) were incubated with $^{125}$I-PDGF (Williams et al., ibid (1982) 79:5067–5070) in the presence of increasing concentrations of AA or BB. Binding was carried out at 37° C. for 45 min. in whole cell suspension. Unbound, radiolabeled PDGF was removed by centrifugation on a Ficoll gradient (Orchansky et al., *J. Immunol.* (1986) 136:169–173). Non-specific binding, determined by incubating CHO cells with $^{125}$I-PDGF, accounted for 25 percent of the bound radioactivity.

The binding study demonstrated that the transfected cells can be used as a model to study the interaction of hPDGF with its receptor. In particular, this study demonstrated that the transfected type B human receptor was functionally identical to the native mouse receptor as indicated by the following results. Both AA and BB forms of PDGF competed for the $^{125}$ I-PDGF labeled sites in the human receptor transfectants. For the transfected type B human receptor as well as the native mouse receptor, the BB form was of higher affinity than the AA form. When expressed in yeast, the AA form of PDGF may be processed aberrantly, giving it a lower affinity than the BB form for both the transfected cells and mouse 3T3 cells. The consistency of the pattern of competition shows that the AA form interacts with the transfected type B human receptor in the same way as it does with the native mouse receptor and demonstrates that these receptors are functionally identical.

Activation of the PDGF Receptor Tyrosine Kinase

The ability of recombinant AA and BB homodimers and of human partially purified AB PDGF to activate the type B receptor tyrosine kinase was studied. The yeast-derived AA and BB homodimeric forms and the platelet-derived AB form stimulated autophosphorylation of the transfected human receptor.

BALB/c 3T3 cells and CHO cells transfected with the human PDGF receptor cDNA (CHO-HR5) were incubated with increasing amounts of the different forms of PDGF (AA, BB and AB). Following polyacrylamide-SDS electrophoresis, the phosphorylated receptor was identified by Western blot using an antiphosphotyrosine antibody (Wang, *Mol. Cell. Biol.* (1985) 5:3640–3643).

The receptor protein co-migrated with the 200 kDa molecular weight marker. The concentration of each form that was effective in stimulating autophosphorylation of the transfected human receptor was identical to the concentration that gave a similar autophosphorylation to the native mouse 3T3 receptor or the transfected mouse receptor.

These results showed for the first time that the AA form of PDGF activates the receptor tyrosine kinase of the type B receptor. Prior to use of the transfected cells, there was no demonstration that the AA form had hPDGF activity or that a single receptor, the type B receptor, was capable of recognizing all three forms of PDGF. Further, the results demonstrate that the human cDNA encodes a type B receptor that is functionally equivalent to the wild-type receptor that is responsible for PDGF-stimulated tyrosine kinase activity in mouse 3T3 cells.

Thus, the transfected cells are useful models for studying PDGF-induced mitogenic responses.

Rate of DNA Synthesis in CHO-Transfected Cells

BALB/c 3T3 cells and CHO cells transfected with the type B human PDGF receptor cDNA (CHO-HR5) were incubated with saturating concentrations of the three forms of PDGF. Untreated cells and cells treated with fetal calf serum (FCS) were used as negative and positive controls, respectively. The level of $^3$H-thymidine incorporation into DNA was determined by measuring the radioactivity of the acid-precipitable material as previously described (Escobedo, supra).

Transfection of CHO cells with either human type B or mouse PDGF receptor conferred a PDGF-sensitive mitogenic response. All forms of PDGF stimulated DNA synthesis in both the type B human receptor transfectant and the mouse cells bearing the native receptor.

These data showed that the A chain homodimer and the B chain homodimer, like the AB platelet-derived form, were mitogens that can act through the receptor encoded by the type B human cDNA sequence. The mitogenic action of these forms of PDGF on mouse 3T3 cells and CHO cells containing the transfected type B human receptor demonstrate that the responses were mediated by functionally identical receptors.

Isolation and Expression of the Type A PDGF Receptor

The type A receptor was isolated as described for the type B receptor, above, except that different probes were used and hybridization and screening were performed under low stringency conditions, as described below. In particular, a region in the type B receptor tyrosine kinase sequence having a high degree of homology to published tyrosine kinase amino acid sequences was identified and had the amino acid sequence (SEQ ID NO: 3), HRDLAARN. Oligonucleotide probes encoding the tyrosine kinase consensus sequence were prepared having the following sequence (SEQ ID NO:4):

GTT(G/C)CGXGCXGCCAGXTC(G/C)CGXTG, where G/C indicates either G or C was used and X indicates any of A, T, C or G was used. The human placenta λGT10 cDNA library was screened as described above but with low stringency conditions using a buffer with 6×SSC 0.1% SDS and 5×Denhardt's solution at 42° C. as follows. Filters were screened by washing at 52° C. in 2×SSC. A clone encoding the type A receptor was isolated and sequenced by the procedure described for the type B receptor gene.

The DNA sequence of the gene encoding the type A receptor (A-hPDGF-R) together with the deduced amino acid sequence are shown in FIG. 2, above.

The clone encoding A-hPDGF-R was digested, gel purified and inserted into the SV40 expression vector, pSV7C, as described for the type B receptor clone.

That vector is used to transfect CHO cells as described above for the type B receptor. With expression of the vector coding sequence, transfected CHO cells produce a functional receptor that binds all three hPDGF isoforms, preferentially binding the AA homodimer.

These studies were made possible by the availability of growth factor preparations devoid of contamination with other growth factors and by the use of a receptor expression system in which all of the measured PDGF responses could be attributed to this single transfected receptor cDNA.

All publications and patent applications herein are incorporated by reference to the same extent as if each individual publication or patent application was specifically and individually indicated to be incorporated by reference. The invention now being full described, it will be apparent to one of ordinary skill in the art that many changes and modifications can be made thereto without departing from the spirit or scope of the appended claims.

What is claimed is:

1. A method of evaluating a drug's ability to function as a human platelet-derived growth factor (hPDGF) receptor agonist or antagonist comprising:

(a) contacting mammalian cells with said drug, which mammalian cells comprise an hPDGF receptor as a result of transfecting said cells with an expression construct comprising a DNA sequence encoding hPDGF-R; and (b) determining the amount of a PDGF-induced response in said cells in comparison to untransfected cells or to a drug providing a known response; and (c) evaluating whether said drug is an agonist or antagonist.

2. The method of claim 1 wherein said expression construct comprises a DNA sequence encoding B-hPDGF-R.

3. The method of claim 1 wherein said expression construct comprises a DNA sequence encoding A-hPDGF-R.

4. The method of claim 1 wherein said expression construct comprises a DNA sequence encoding A-hPDGF-R and B-hPDGF-R.

5. The method of claim 1, wherein the PDGF-induced response is determined by measuring DNA synthesis in said cells.

6. The method of claim 1, wherein the PDGF-induced response is determined by measuring hPDGF receptor tyrosine kinase activity in said cells.

7. A method of evaluating a drug's ability to function as a human platelet-derived growth factor (hPDGF) receptor agonist or antagonist comprising:

(a) contacting mammalian cells with said drug, which mammalian cells comprise an hPDGF receptor as a result of transfecting said cells with an expression construct comprising a DNA sequence encoding hPDGF-R wherein said DNA sequence is SEQ ID NO: 1 or SEQ ID NO:2; and (b) determining the amount of a PDGF-induced response in said cells in comparison to untransfected cells or to a drug providing a known response; and (c) evaluating whether said drug is an agonist or antagonist.

8. The method of claim 7 wherein said expression construct comprises a DNA sequence encoding A-hPDGF-R, wherein said DNA sequence is SEQ ID NO:2.

9. The method of claim 7 wherein said expression construct comprises a DNA sequence encoding A-hPDGF-R, wherein said A-hPDGF-encoding sequence is SEQ ID NO:2, and a DNA sequence encoding B-hPDGF-R, wherein said B-hPDGF-encoding sequence is SEQ ID NO:1.

10. The method of claim 7, wherein the PDGF-induced response is determined by measuring DNA synthesis in said cells.

11. The method of claim 7, wherein the PDGF-induced response is determined by measuring the receptor tyrosine kinase activity in said cells.

12. A method of evaluating a drug's ability to function as a human platelet-derived growth factor (hPDGF) receptor agonist or antagonist comprising:

(a) contacting mammalian cells with said drug, which mammalian cells comprise an hPDGF receptor as a result of transfecting said cells with an expression construct comprising a DNA sequence encoding hPDGF-R wherein said DNA sequence is SEQ ID NO: 1; and (b) determining the amount of a PDGF-induced response in said cells in comparison to untransfected cells or to a drug providing a known response; and (c) evaluating whether said drug is an agonist or antagonist.

\* \* \* \* \*

UNITED STATES PATENT AND TRADEMARK OFFICE
CERTIFICATE OF CORRECTION

PATENT NO. : 6,566,075 B1  
DATED : May 20, 2003  
INVENTOR(S) : Jaime Escobedo et al.

It is certified that error appears in the above-identified patent and that said Letters Patent is hereby corrected as shown below:

Column 1,
Line 4, insert the following:

-- This invention was made with Government support under Grant No. HL32898, awarded by the National Institutes of Health. The Government has certain rights in this invention. --

Signed and Sealed this

Seventh Day of October, 2003

JAMES E. ROGAN
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 5727 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 463..3783

(ix) FEATURE:
      (A) NAME/KEY: sig_peptide
      (B) LOCATION: 463..558

(ix) FEATURE:
      (A) NAME/KEY: mat_peptide
      (B) LOCATION: 561..3783

(xi) SEQUENCE DESCRIPTION: SEQ ID NO: 1:

```
CGCTGGCTGC TGGCAGCAGA GTGACTGCCC GCCCTATCTG GGACCCAGGA TCGCTCTGTG      60

AGCAACTTGG AGCCAGAGAG GAGATCAACA AGGAGGAGGA GAGAGCCGGC CCCTCAGCC      120

TGCTGCCCAG CAGCAGCCTG TGCTCGCCCT GCCCAACGCA GACAGCCAGA CCCAGGGCG      180

CCCCTCTGGC GGCTCTGCTC CTCCGAAGAT GCTTGGGGAG TGAGGCGACA TGGGGCCGC      240

CCTCTCCCCT ACAGCAGCCC CCTTCCTCCA TCCCTCTGTT CTCCTGAGCC TTCAGGAGC      300

TGCACCAGTC CTGCCTGTCC TTCTACTCAG CTGTTACCCA CTCTGGGACC AGCAGTCTT      360

CTGATAACTG GGAGAGGGCA GTAAGGAGGA CTTCCTGGAG GGGGTGACTG TCCAGAGCC      420

GGAACTGTGC CCACACCAGA AGCCATCAGC AGCAAGGACA CC ATG CGG CTT CCG         474
                                              Met Arg Leu Pro
                                              -32     -30
```

```
GGT GCG ATG CCA GCT CTG GCC CTC AAA GGC GAG CTG CTG TTG CTG TCT      522
Gly Ala Met Pro Ala Leu Ala Leu Lys Gly Glu Leu Leu Leu Leu Ser
        -25             -20                 -15

CTC CTG TTA CTT CTG GAA CCA CAG ATC TCT CAG GGC CTG GTC GTC ACA      570
Leu Leu Leu Leu Leu Glu Pro Gln Ile Ser Gln Gly Leu Val Val Thr
            -10             -5                  1

CCC CCG GGG CCA GAG CTT GTC CTC AAT GTC TCC AGC ACC TTC GTT CTG      618
Pro Pro Gly Pro Glu Leu Val Leu Asn Val Ser Ser Thr Phe Val Leu
 5               10                  15                      20

ACC TGC TCG GGT TCA GCT CCG GTG GTG TGG GAA CGG ATG TCC CAG GAG      666
Thr Cys Ser Gly Ser Ala Pro Val Val Trp Glu Arg Met Ser Gln Glu
                 25              30                  35

CCC CCA CAG GAA ATG GCC AAG GCC CAG GAT GGC ACC TTC TCC AGC GTG      714
Pro Pro Gln Glu Met Ala Lys Ala Gln Asp Gly Thr Phe Ser Ser Val
         40                  45                  50

CTC ACA CTG ACC AAC CTC ACT GGG CTA GAC ACG GGA GAA TAC TTT TGC      762
Leu Thr Leu Thr Asn Leu Thr Gly Leu Asp Thr Gly Glu Tyr Phe Cys
             55                  60                  65

ACC CAC AAT GAC TCC CGT GGA CTG GAG ACC GAT GAG CGG AAA CGG CTC      810
Thr His Asn Asp Ser Arg Gly Leu Glu Thr Asp Glu Arg Lys Arg Leu
         70                  75                  80

TAC ATC TTT GTG CCA GAT CCC ACC GTG GGC TTC CTC CCT AAT GAT GCC      858
Tyr Ile Phe Val Pro Asp Pro Thr Val Gly Phe Leu Pro Asn Asp Ala
 85                  90                  95                 100

GAG GAA CTA TTC ATC TTT CTC ACG GAA ATA ACT GAG ATC ACC ATT CCA      906
Glu Glu Leu Phe Ile Phe Leu Thr Glu Ile Thr Glu Ile Thr Ile Pro
                105                 110                 115

TGC CGA GTA ACA GAC CCA CAG CTG GTG GTG ACA CTG CAC GAG AAG AAA      954
Cys Arg Val Thr Asp Pro Gln Leu Val Val Thr Leu His Glu Lys Lys
                120                 125                 130

GGG GAC GTT GCA CTG CCT GTC CCC TAT GAT CAC CAA CGT GGC TTT TCT      1002
Gly Asp Val Ala Leu Pro Val Pro Tyr Asp His Gln Arg Gly Phe Ser
                135                 140                 145

GGT ATC TTT GAG GAC AGA AGC TAC ATC TGC AAA ACC ACC ATT GGG GAC      1050
Gly Ile Phe Glu Asp Arg Ser Tyr Ile Cys Lys Thr Thr Ile Gly Asp
        150                 155                 160

AGG GAG GTG GAT TCT GAT GCC TAC TAT GTC TAC AGA CTC CAG GTG TCA      1098
Arg Glu Val Asp Ser Asp Ala Tyr Tyr Val Tyr Arg Leu Gln Val Ser
165                 170                 175                 180

TCC ATC AAC GTC TCT GTG AAC GCA GTG CAG ACT GTG GTC CGC CAG GGT      1146
Ser Ile Asn Val Ser Val Asn Ala Val Gln Thr Val Val Arg Gln Gly
                185                 190                 195

GAG AAC ATC ACC CTC ATG TGC ATT GTG ATC GGG AAT GAG GTG GTC AAC      1194
Glu Asn Ile Thr Leu Met Cys Ile Val Ile Gly Asn Glu Val Val Asn
```

-continued

```
                200                 205                 210
TTC GAG TGG ACA TAC CCC CGC AAA GAA AGT GGG CGG CTG GTG GAG CCG    1242
Phe Glu Trp Thr Tyr Pro Arg Lys Glu Ser Gly Arg Leu Val Glu Pro
            215                 220                 225

GTG ACT GAC TTC CTC TTG GAT ATG CCT TAC CAC ATC CGC TCC ATC CTG    1290
Val Thr Asp Phe Leu Leu Asp Met Pro Tyr His Ile Arg Ser Ile Leu
        230                 235                 240

CAC ATC CCC AGT GCC GAG TTA GAA GAC TCG GGG ACC TAC ACC TGC AAT    1338
His Ile Pro Ser Ala Glu Leu Glu Asp Ser Gly Thr Tyr Thr Cys Asn
245                 250                 255                 260

GTG ACG GAG AGT GTG AAT GAC CAT CAG GAT GAA AAG GCC ATC AAC ATC    1386
Val Thr Glu Ser Val Asn Asp His Gln Asp Glu Lys Ala Ile Asn Ile
            265                 270                 275

ACC GTG GTT GAG AGC GGC TAC GTG CGG CTC CTG GGA GAG GTG GGC ACA    1434
Thr Val Val Glu Ser Gly Tyr Val Arg Leu Leu Gly Glu Val Gly Thr
        280                 285                 290

CTA CAA TTT GCT GAG CTG CAT CGG AGC CGG ACA CTG CAG GTA GTG TTC    1482
Leu Gln Phe Ala Glu Leu His Arg Ser Arg Thr Leu Gln Val Val Phe
            295                 300                 305

GAG GCC TAC CCA CCG CCC ACT GTC CTG TGG TTC AAA GAC AAC CGC ACC    1530
Glu Ala Tyr Pro Pro Pro Thr Val Leu Trp Phe Lys Asp Asn Arg Thr
            310                 315                 320

CTG GGC GAC TCC AGC GCT GGC GAA ATC GCC CTG TCC ACG CGC AAC GTG    1578
Leu Gly Asp Ser Ser Ala Gly Glu Ile Ala Leu Ser Thr Arg Asn Val
325                 330                 335                 340

TCG GAG ACC CGG TAT GTG TCA GAG CTG ACA CTG GTT CGC GTG AAG GTG    1626
Ser Glu Thr Arg Tyr Val Ser Glu Leu Thr Leu Val Arg Val Lys Val
            345                 350                 355

GCA GAG GCT CGC CAC TAC ACC ATG CGG GCC TTC CAT GAG GAT GCT GAG    1674
Ala Glu Ala Arg His Tyr Thr Met Arg Ala Phe His Glu Asp Ala Glu
            360                 365                 370

GTC CAG CTC TCC TTC CAG CTA CAG ATC AAT GTC CCT GTC CGA GTG CTG    1722
Val Gln Leu Ser Phe Gln Leu Gln Ile Asn Val Pro Val Arg Val Leu
            375                 380                 385

GAG CTA AGT GAG AGC CAC CCT GAC AGT GGG GAA CAG ACA GTC CGC TGT    1770
Glu Leu Ser Glu Ser His Pro Asp Ser Gly Glu Gln Thr Val Arg Cys
            390                 395                 400

CGT GGC CGG GGC ATG CCC CAG CCG AAC ATC ATC TGG TCT GCC TGC AGA    1818
Arg Gly Arg Gly Met Pro Gln Pro Asn Ile Ile Trp Ser Ala Cys Arg
405                 410                 415                 420

GAC CTC AAA AGG TGT CCA CGT GAG CTG CCG CCC ACG CTG CTG GGG AAC    1866
Asp Leu Lys Arg Cys Pro Arg Glu Leu Pro Pro Thr Leu Leu Gly Asn
            425                 430                 435

AGT TCC GAA GAG GAG ACC CAG CTG GAG ACT AAC GTG ACG TAC TGG GAG    1914
Ser Ser Glu Glu Glu Thr Gln Leu Glu Thr Asn Val Thr Tyr Trp Glu
            440                 445                 450

GAG GAG CAG GAG TTT GAG GTG GTG AGC ACA CTG CGT CTG CAG CAC GTG    1962
Glu Glu Gln Glu Phe Glu Val Val Ser Thr Leu Arg Leu Gln His Val
            455                 460                 465

GAT CGG CCA CTG TCG GTG CGC TGC ACG CTG CGC AAC GCT GTG GGC CAG    2010
Asp Arg Pro Leu Ser Val Arg Cys Thr Leu Arg Asn Ala Val Gly Gln
            470                 475                 480

GAC ACG CAG GAG GTC ATC GTG GTG CCA CAC TCC TTG CCC TTT AAG GTG    2058
Asp Thr Gln Glu Val Ile Val Val Pro His Ser Leu Pro Phe Lys Val
485                 490                 495                 500

GTG GTG ATC TCA GCC ATC CTG GCC CTG GTG GTG CTC ACC ATC ATC TCC    2106
Val Val Ile Ser Ala Ile Leu Ala Leu Val Val Leu Thr Ile Ile Ser
            505                 510                 515

CTT ATC ATC CTC ATC ATG CTT TGG CAG AAG AAG CCA CGT TAC GAG ATC    2154
```

-continued

```
            Leu Ile Ile Leu Ile Met Leu Trp Gln Lys Lys Pro Arg Tyr Glu Ile
                        520                 525                 530

CGA TGG AAG GTG ATT GAG TCT GTG AGC TCT GAC GGC CAT GAG TAC ATC                 2202
Arg Trp Lys Val Ile Glu Ser Val Ser Ser Asp Gly His Glu Tyr Ile
            535                 540                 545

TAC GTG GAC CCC ATG CAG CTG CCC TAT GAC TCC ACG TGG GAG CTG CCG                 2250
Tyr Val Asp Pro Met Gln Leu Pro Tyr Asp Ser Thr Trp Glu Leu Pro
550                 555                 560

CGG GAC CAG CTT GTG CTG GGA CGC ACC CTC GGC TCT GGG GCC TTT GGG                 2298
Arg Asp Gln Leu Val Leu Gly Arg Thr Leu Gly Ser Gly Ala Phe Gly
565                 570                 575                 580

CAG GTG GTG GAG GCC ACG GCT CAT GGC CTG AGC CAT TCT CAG GCC ACG                 2346
Gln Val Val Glu Ala Thr Ala His Gly Leu Ser His Ser Gln Ala Thr
            585                 590                 595

ATG AAA GTG GCC GTC AAG ATG CTT AAA TCC ACA GCC CGC AGC AGT GAG                 2394
Met Lys Val Ala Val Lys Met Leu Lys Ser Thr Ala Arg Ser Ser Glu
            600                 605                 610

AAG CAA GCC CTT ATG TCG GAG CTG AAG ATC ATG AGT CAC CTT GGG CCC                 2442
Lys Gln Ala Leu Met Ser Glu Leu Lys Ile Met Ser His Leu Gly Pro
            615                 620                 625

CAC CTG AAC GTG GTC AAC CTG TTG GGG GCC TGC ACC AAA GGA GGA CCC                 2490
His Leu Asn Val Val Asn Leu Leu Gly Ala Cys Thr Lys Gly Gly Pro
            630                 635                 640

ATC TAT ATC ATC ACT GAG TAC TGC CGC TAC GGA GAC CTG GTG GAC TAC                 2538
Ile Tyr Ile Ile Thr Glu Tyr Cys Arg Tyr Gly Asp Leu Val Asp Tyr
645                 650                 655                 660

CTG CAC CGC AAC AAA CAC ACC TTC CTG CAG CAC CAC TCC GAC AAG CGC                 2586
Leu His Arg Asn Lys His Thr Phe Leu Gln His His Ser Asp Lys Arg
                        665                 670                 675

CGC CCG CCC AGC GCG GAG CTC TAC AGC AAT GCT CTG CCC GTT GGG GTC                 2634
Arg Pro Pro Ser Ala Glu Leu Tyr Ser Asn Ala Leu Pro Val Gly Val
                        680                 685                 690

CCC CTG CCC AGC CAT GTG TCC TTG ACC GGG GAG AGC GAC GGT GGC TAC                 2682
Pro Leu Pro Ser His Val Ser Leu Thr Gly Glu Ser Asp Gly Gly Tyr
            695                 700                 705

ATG GAC ATG AGC AAG GAC GAG TCG GTG GAC TAT GTG CCC ATG CTG GAC                 2730
Met Asp Met Ser Lys Asp Glu Ser Val Asp Tyr Val Pro Met Leu Asp
            710                 715                 720

ATG AAA GGA GAC GTC AAA TAT GCA GAC ATC GAG TCC TCC AAC TAC ATG                 2778
Met Lys Gly Asp Val Lys Tyr Ala Asp Ile Glu Ser Ser Asn Tyr Met
725                 730                 735                 740

GCG CCT TAC GAT AAC TAC GTT CCC TCT GCC CCT GAG AGG ACC TGC CGA                 2826
Ala Pro Tyr Asp Asn Tyr Val Pro Ser Ala Pro Glu Arg Thr Cys Arg
                        745                 750                 755

GCA ACT TTG ATC AAC GAG TCT CCA GTG CTA AGC TAC ATG GAC CTC GTG                 2874
Ala Thr Leu Ile Asn Glu Ser Pro Val Leu Ser Tyr Met Asp Leu Val
            760                 765                 770

GGC TTC AGC TAC CAG GTG GCC AAT GGC ATG GAG TTT CTG GCC TCC AAG                 2922
Gly Phe Ser Tyr Gln Val Ala Asn Gly Met Glu Phe Leu Ala Ser Lys
            775                 780                 785

AAC TGC GTC CAC AGA GAC CTG GCG GCT AGG AAC GTG CTC ATC TGT GAA                 2970
Asn Cys Val His Arg Asp Leu Ala Ala Arg Asn Val Leu Ile Cys Glu
            790                 795                 800

GGC AAG CTG GTC AAG ATC TGT GAC TTT GGC CTG GCT CGA GAC ATC ATG                 3018
Gly Lys Leu Val Lys Ile Cys Asp Phe Gly Leu Ala Arg Asp Ile Met
805                 810                 815                 820

CGG GCC TCG AAT TAC ATC TCC AAA GGC AGC ACC TTT TTG CCT TTA AAG                 3066
Arg Ala Ser Asn Tyr Ile Ser Lys Gly Ser Thr Phe Leu Pro Leu Lys
                        825                 830                 835
```

```
TGG ATG GCT CCG GAG AGC ATC TTC AAC AGC CTC TAC ACC ACC CTG AGC    3114
Trp Met Ala Pro Glu Ser Ile Phe Asn Ser Leu Tyr Thr Thr Leu Ser
        840                 845                 850

GAC GTG TGG TCC TTC GGG ATC CTG CTC TGG GAG ATC TTC ACC TTG GGT    3162
Asp Val Trp Ser Phe Gly Ile Leu Leu Trp Glu Ile Phe Thr Leu Gly
            855                 860                 865

GGC ACC CCT TAC CCA GAG CTG CCC ATG AAC GAG CAG TTC TAC AAT GCC    3210
Gly Thr Pro Tyr Pro Glu Leu Pro Met Asn Glu Gln Phe Tyr Asn Ala
        870                 875                 880

ATC AAA CGG GGT TAC CGC ATG GCC CAG CCT GCC CAT GCC TCC GAC GAG    3258
Ile Lys Arg Gly Tyr Arg Met Ala Gln Pro Ala His Ala Ser Asp Glu
885                 890                 895                 900

ATC TAT GAG ATC ATG CAG AAG TGC TGG GAA GAG AAG TTT GAG ATT CGG    3306
Ile Tyr Glu Ile Met Gln Lys Cys Trp Glu Glu Lys Phe Glu Ile Arg
            905                 910                 915

CCC CCC TTC TCC CAG CTG GTG CTG CTT CTC GAG AGA CTG TTG GGC GAA    3354
Pro Pro Phe Ser Gln Leu Val Leu Leu Leu Glu Arg Leu Leu Gly Glu
            920                 925                 930

GGT TAC AAA AAG AAG TAC CAG CAG GTG GAT GAG GAG TTT CTG AGG AGT    3402
Gly Tyr Lys Lys Lys Tyr Gln Gln Val Asp Glu Glu Phe Leu Arg Ser
        935                 940                 945

GAC CAC CCA GCC ATC CTT CGG TCC CAG GCC CGC TTG CCT GGG TTC CAT    3450
Asp His Pro Ala Ile Leu Arg Ser Gln Ala Arg Leu Pro Gly Phe His
        950                 955                 960

GGC CTC CGA TCT CCC CTG GAC ACC AGC TCC GTC CTC TAT ACT GCC GTG    3498
Gly Leu Arg Ser Pro Leu Asp Thr Ser Ser Val Leu Tyr Thr Ala Val
965                 970                 975                 980

CAG CCC AAT GAG GGT GAC AAC GAC TAT ATC ATC CCC CTG CCT GAC CCC    3546
Gln Pro Asn Glu Gly Asp Asn Asp Tyr Ile Ile Pro Leu Pro Asp Pro
            985                 990                 995

AAA CCC GAG GTT GCT GAC GAG GGC CCA CTG GAG GGT TCC CCC AGC CTA    3594
Lys Pro Glu Val Ala Asp Glu Gly Pro Leu Glu Gly Ser Pro Ser Leu
            1000                1005                1010

GCC AGC TCC ACC CTG AAT GAA GTC AAC ACC TCC TCA ACC ATC TCC TGT    3642
Ala Ser Ser Thr Leu Asn Glu Val Asn Thr Ser Ser Thr Ile Ser Cys
        1015                1020                1025

GAC AGC CCC CTG GAG CCC CAG GAC GAA CCA GAG CCA GAG CCC CAG CTT    3690
Asp Ser Pro Leu Glu Pro Gln Asp Glu Pro Glu Pro Glu Pro Gln Leu
        1030                1035                1040

GAG CTC CAG GTG GAG CCG GAG CCA GAG CTG GAA CAG TTG CCG GAT TCG    3738
Glu Leu Gln Val Glu Pro Glu Pro Glu Leu Glu Gln Leu Pro Asp Ser
1045                1050                1055                1060

GGG TGC CCT GCG CCT CGG GCT GAA GCA GAG GAT AGC TTC CTG TAG        3783
Gly Cys Pro Ala Pro Arg Ala Glu Ala Glu Asp Ser Phe Leu  *
                1065                1070                1075

GGGGCTGGCC CCTACCCTGC CCTGCCTGAA GCTCCCCCCC TGCCAGCACC CAGCATCT    3843

TGGCCTGGCC TGACCGGGCT TCCTGTCAGC CAGGCTGCCC TTATCAGCTG TCCCCTTC    3903

GAAGCTTTCT GCTCCTGACG TGTTGTGCCC CAAACCCTGG GGCTGGCTTA GGAGGCAA    3963

AAACTGCAGG GGCCGTGACC AGCCCTCTGC CTCCAGGGAG GCCAACTGAC TCTGAGCC    4023

GGTTCCCCCA GGGAACTCAG TTTTCCCATA TGTAAAATGG GAAAGTTAGG CTTGATGA    4083

CAGAATCTAG GATTCTCTCC CTGGCTGACA GGTGGGGAGA CCGAATCCCT CCCTGGGA    4143

ATTCTTGGAG TTACTGAGGT GGTAAATTAA CTTTTTTCTG TTCAGCCAGC TACCCCTC    4203

GGAATCATAG CTCTCTCCTC GACTTTATCC ACCCAGGAGC TAGGGAAGAG ACCCTAGC    4263

CCCTGGCTGC TGGCTGAGCT AGGGCCTAGC CTTGAGCAGT GTTGCCTCAT CCAGAAGA    4323

CCAGTCTCCT CCCTATGATG GCCAGTAAAT GCGTTCCCTG GCCCGAGCTG GTCTGGGG    4383
```

-continued

```
ATTAGGCAGC CTAATTAATG CTGGAGGCTG AGCCAAGTAC AGGACACCCC CAGCCTGC     4443

CCCTTGCCCA GGGCACTTGG AGCACACGCA CCATAGCAAG TCCTGTGTCC CTGTCCTT     4503

GGCCCATCAG TCCTGGGGCT TTTTCTTTAT CACCCTCAGT CTTAATCCAT CCACCAGA     4563

CTAGAAGGCC AGACGGGCCC CGCATCTGTG ATGAGAATGT AAATGTGCCA GTGTGGAG     4623

GCCACGTGTG TGTGCCAGTA TATGGCCCTG GCTCTGCATT GGACCTGCTA TGAGGCTT     4683

GAGGAATCCC TCACCCTCTC TGGGCCTCAG TTTCCCCTTC AAAAAATGAA TAAGTCGG     4743

TTATTAACTC TGATGCCTTG CCAGCACTAA CATTCTAGAG TATTCCAGGT GGTTGCAC     4803

TTGTCCAGAT GAAGCAAGGC CATATACCCT AAACTTCCAT CCTGGGGGTC AGCTGGGC     4863

CTGGGAGATT CCAGATCACA CATCACACTC TGGGGACTCA GGAACCATGC CCCTTCCC     4923

GGCCCCCAGC AAGTCTCAAG AACACAGCTG CACAGGCCTT GACTTAGAGT GACAGCCG     4983

GTCCTGGAAA GCCCCAGCA GCTGCCCAG GACATGGGAA GACCACGGGA CCTCTTTC     5043

TACCCACGAT GACCTCCGGG GGTATCCTGG GCAAAAGGGA CAAAGAGGGC AAATGAGA     5103

ACCTCCTGCA GCCCACCACT CCAGCACCTG TGCCGAGGTC TGCGTCGAAG ACAGAATG     5163

CAGTGAGGAC AGTTATGTCT TGGAAAAGAC AAGAAGCCTC AGAGTGGGTA CCCCAAGA     5223

GATGTGAGAG GTGGGCGCTT TGGAGGTTTG CCCCTCACCC ACCAGCTGCC CCATCCCT     5283

GGCAGCGCTC CATGGGGGTA TGGTTTTGTC ACTGCCCAGA CCTAGCAGTG ACATCTCA     5343

GTCCCCAGCC CAGTGGGCAT TGGAGGTGCC AGGGGAGTCA GGGTTGTAGC CAAGACGC     5403

GCACGGGGAG GGTTGGGAAG GGGGTGCAGG AAGCTCAACC CCTCTGGCAC CAACCCTG     5463

TTGCAGTTGG CACCTTACTT CCCTGGGATC CCCAGAGTTG GTCCAAGGAG GGAGAGTG     5523

TTCTCAATAC GGTACCAAAG ATATAATCAC CTAGGTTTAC AAATATTTTT AGGACTCA     5583

TTAACTCACA TTTATACAGC AGAAATGCTA TTTTGTGATG CTGTTAAGTT TTTCTATC     5643

TGTACTTTTT TTTAAGGGAA AGATTTTAAT ATTAAACCTG GTCTTCTCAA AAAAAAAA     5703

AAAAAAAAAA AAAAAAAAAA AAAA                                         5727
```

(2) INFORMATION FOR SEQ ID NO: 2:

(i) SEQUENCE CHARACTERISTICS:
       (A) LENGTH: 3199 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 2..3199

(xi) SEQUENCE DESCRIPTION: SEQ ID NO: 2:

```
A AAT GAA AAG GTT GTG CAG CTG AAT TCA TCC TTT TCT CTG AGA TGC            46
  Asn Glu Lys Val Val Gln Leu Asn Ser Ser Phe Ser Leu Arg Cys
              1080            1085            1090

TTT GGG GAG AGT GAA GTG AGC TGG CAG TAC CCC ATG TCT GAA GAA GAG          94
Phe Gly Glu Ser Glu Val Ser Trp Gln Tyr Pro Met Ser Glu Glu Glu
            1095            1100            1105

AGC TCC GAT GTG GAA ATC AGA AAT GAA GAA AAC AAC AGC GGC CTT TCT         142
Ser Ser Asp Val Glu Ile Arg Asn Glu Glu Asn Asn Ser Gly Leu Ser
            1110            1115            1120

GTG ACG GTC TTG GAA GTG AGC AGT GCC TCG GCG GCC CAC ACA GGG TTG         190
Val Thr Val Leu Glu Val Ser Ser Ala Ser Ala Ala His Thr Gly Leu
        1125            1130            1135
```

```
TAC ACT TGC TAT TAC AAC CAC ACT CAG ACA GAA GAG AAT GAG CTT GAA     238
Tyr Thr Cys Tyr Tyr Asn His Thr Gln Thr Glu Glu Asn Glu Leu Glu
        1140                1145                1150

GGC AGG CAC ATT TAC ATC TAT GTG CCA GAC CCA GAT GTA GCC TTT GTA     286
Gly Arg His Ile Tyr Ile Tyr Val Pro Asp Pro Asp Val Ala Phe Val
1155                1160                1165                1170

CCT CTA GGA ATG ACG GAT TAT TTA GTC ATC GTG GAG GAT GAT GAT TCT     334
Pro Leu Gly Met Thr Asp Tyr Leu Val Ile Val Glu Asp Asp Asp Ser
                1175                1180                1185

GCC ATT ATA CCT TGT CGC ACA ACT GAT CCC GAG ACT CCT GTA ACC TTA     382
Ala Ile Ile Pro Cys Arg Thr Thr Asp Pro Glu Thr Pro Val Thr Leu
            1190                1195                1200

CAC AAC AGT GAG GGG GTG GTA CCT GCC TCC TAC GAC AGC AGA CAG GGC     430
His Asn Ser Glu Gly Val Val Pro Ala Ser Tyr Asp Ser Arg Gln Gly
        1205                1210                1215

TTT AAT GGG ACC TTC ACT GTA GGG CCC TAT ATC TGT GAG GCC ACC GTC     478
Phe Asn Gly Thr Phe Thr Val Gly Pro Tyr Ile Cys Glu Ala Thr Val
    1220                1225                1230

AAA GGA AAG AAG TTC CAG ACC ATC CCA TTT AAT GTT TAT GCT TTA AAA     526
Lys Gly Lys Lys Phe Gln Thr Ile Pro Phe Asn Val Tyr Ala Leu Lys
1235                1240                1245                1250

GCA ACA TCA GAG CTG GAT CTA GAA ATG GAA GCT CTT AAA ACC GTG TAT     574
Ala Thr Ser Glu Leu Asp Leu Glu Met Glu Ala Leu Lys Thr Val Tyr
                1255                1260                1265

AAG TCA GGG GAA ACG ATT GTG GTC ACC TGT GCT GTT TTT AAC AAT GAG     622
Lys Ser Gly Glu Thr Ile Val Val Thr Cys Ala Val Phe Asn Asn Glu
            1270                1275                1280

GTG GTT GAC CTT CAA TGG ACT TAC CCT GGA GAA GTG AAA GGC AAA GGC     670
Val Val Asp Leu Gln Trp Thr Tyr Pro Gly Glu Val Lys Gly Lys Gly
        1285                1290                1295

ATC ACA ATG CTG GAA GAA ATC AAA GTC CCA TCC ATC AAA TTG GTG TAC     718
Ile Thr Met Leu Glu Glu Ile Lys Val Pro Ser Ile Lys Leu Val Tyr
    1300                1305                1310

ACT TTG ACG GTC CCC GAG GCC ACG GTG AAA GAC AGT GGA GAT TAC GAA     766
Thr Leu Thr Val Pro Glu Ala Thr Val Lys Asp Ser Gly Asp Tyr Glu
1315                1320                1325                1330

TGT GCT GCC CGC CAG GCT ACC AGG GAG GTC AAA GAA ATG AAG AAA GTC     814
Cys Ala Ala Arg Gln Ala Thr Arg Glu Val Lys Glu Met Lys Lys Val
                1335                1340                1345

ACT ATT TCT GTC CAT GAG AAA GGT TTC ATT GAA ATC AAA CCC ACC TTC     862
Thr Ile Ser Val His Glu Lys Gly Phe Ile Glu Ile Lys Pro Thr Phe
            1350                1355                1360

AGC CAG TTG GAA GCT GTC AAC CTG CAT GAA GTC AAA CAT TTT GTT GTA     910
Ser Gln Leu Glu Ala Val Asn Leu His Glu Val Lys His Phe Val Val
        1365                1370                1375

GAG GTG CGG GCC TAC CCA CCT CCC AGG ATA TCC TGG CTG AAA AAC AAT     958
Glu Val Arg Ala Tyr Pro Pro Pro Arg Ile Ser Trp Leu Lys Asn Asn
    1380                1385                1390

CTG ACT CTG ATT GAA AAT CTC ACT GAG ATC ACC ACT GAT GTG GAA AAG    1006
Leu Thr Leu Ile Glu Asn Leu Thr Glu Ile Thr Thr Asp Val Glu Lys
1395                1400                1405                1410

ATT CAG GAA ATA AGG TAT CGA AGC AAA TTA AAG CTG ATC CGT GCT AAC    1054
Ile Gln Glu Ile Arg Tyr Arg Ser Lys Leu Lys Leu Ile Arg Ala Asn
                1415                1420                1425

CAA GAA GAC AGT GGC CAT TAT ACT ATT GTA GCT CAA AAT GAA GAT GCT    1102
Gln Glu Asp Ser Gly His Tyr Thr Ile Val Ala Gln Asn Glu Asp Ala
            1430                1435                1440

GTG AAG AGC TAT ACT TTT GAA CTG TTA ACT CAA GTT CCT TCA TCC ATT    1150
Val Lys Ser Tyr Thr Phe Glu Leu Leu Thr Gln Val Pro Ser Ser Ile
```

-continued

```
            1445                  1450                  1455
CTG GAC TTG GTC GAT GAT CAC CAT GGC TCA ACT GGG GGA CAG ACG GTG        1198
Leu Asp Leu Val Asp Asp His His Gly Ser Thr Gly Gly Gln Thr Val
    1460                  1465                  1470

AGG TGC ACA GCT GAA GGC ACG CCG CTT CCT GAT ATT GAG TGG ATG ATA        1246
Arg Cys Thr Ala Glu Gly Thr Pro Leu Pro Asp Ile Glu Trp Met Ile
1475                  1480                  1485                  1490

TGC AAA GAT ATT AAG AAA TGT AAT AAT GAA ACT TCC TGG ACT ATT TTG        1294
Cys Lys Asp Ile Lys Lys Cys Asn Asn Glu Thr Ser Trp Thr Ile Leu
            1495                  1500                  1505

GCC AAC AAT GTC TCA AAC ATC ATC ACG GAG ATC CAC TCC CGA GAC AGG        1342
Ala Asn Asn Val Ser Asn Ile Ile Thr Glu Ile His Ser Arg Asp Arg
        1510                  1515                  1520

AGT ACC GTG GAG GGC CGT GTG ACT TTC GCC AAA GTG GAG GAG ACC ATC        1390
Ser Thr Val Glu Gly Arg Val Thr Phe Ala Lys Val Glu Glu Thr Ile
            1525                  1530                  1535

GCC GTG CGA TGC CTG GCT AAG AAT CTC CTT GGA GCT GAG AAC CGA GAG        1438
Ala Val Arg Cys Leu Ala Lys Asn Leu Leu Gly Ala Glu Asn Arg Glu
        1540                  1545                  1550

CTG AAG CTG GTG GCT CCC ACC CTG CGT TCT GAA CTC ACG GTG GCT GCT        1486
Leu Lys Leu Val Ala Pro Thr Leu Arg Ser Glu Leu Thr Val Ala Ala
1555                  1560                  1565                  1570

GCA GTC CTG GTG CTG TTG GTG ATT GTG ATC ATC TCA CTT ATT GTC CTG        1534
Ala Val Leu Val Leu Leu Val Ile Val Ile Ile Ser Leu Ile Val Leu
                1575                  1580                  1585

GTT GTC ATT TGG AAA CAG AAA CCG AGG TAT GAA ATT CGC TGG AGG GTC        1582
Val Val Ile Trp Lys Gln Lys Pro Arg Tyr Glu Ile Arg Trp Arg Val
                1590                  1595                  1600

ATT GAA TCA ATC AGC CCG GAT GGA CAT GAA TAT ATT TAT GTG GAC CCG        1630
Ile Glu Ser Ile Ser Pro Asp Gly His Glu Tyr Ile Tyr Val Asp Pro
            1605                  1610                  1615

ATG CAG CTG CCT TAT GAC TCA AGA TGG GAG TTT CCA AGA GAT GGA CTA        1678
Met Gln Leu Pro Tyr Asp Ser Arg Trp Glu Phe Pro Arg Asp Gly Leu
        1620                  1625                  1630

GTG CTT GGT CGG GTC TTG GGG TCT GGA GCG TTT GGG AAG GTG GTT GAA        1726
Val Leu Gly Arg Val Leu Gly Ser Gly Ala Phe Gly Lys Val Val Glu
1635                  1640                  1645                  1650

GGA ACA GCC TAT GGA TTA AGC CGG TCC CAA CCT GTC ATG AAA GTT GCA        1774
Gly Thr Ala Tyr Gly Leu Ser Arg Ser Gln Pro Val Met Lys Val Ala
                1655                  1660                  1665

GTG AAC ATG CTA AAA CCC ACG GCC AGA TCC AGT GAA AAA CAA GCT CTC        1822
Val Asn Met Leu Lys Pro Thr Ala Arg Ser Ser Glu Lys Gln Ala Leu
            1670                  1675                  1680

ATG TCT GAA CTG AAG ATA ATG ACT CAC CTG GGG CCA CAT TTG AAC ATT        1870
Met Ser Glu Leu Lys Ile Met Thr His Leu Gly Pro His Leu Asn Ile
        1685                  1690                  1695

GTA AAC TTG CTG GGA GCC TGC ACC AAG TCA GGC CCC ATT TAC ATC ATC        1918
Val Asn Leu Leu Gly Ala Cys Thr Lys Ser Gly Pro Ile Tyr Ile Ile
    1700                  1705                  1710

ACA GAG TAT TGC TTC TAT GGA GAT TTG GTC AAC TAT TTG CAT AAG AAT        1966
Thr Glu Tyr Cys Phe Tyr Gly Asp Leu Val Asn Tyr Leu His Lys Asn
1715                  1720                  1725                  1730

AGG GAT AGC TTC CTG AGC CAC CAC CCA GAG AAG CCA AAG AAA GAG CTG        2014
Arg Asp Ser Phe Leu Ser His His Pro Glu Lys Pro Lys Lys Glu Leu
                1735                  1740                  1745

GAT ATC TTT GGA TTG AAC CCT GCT GAT GAA AGC ACA CGG AGC TAT GTT        2062
Asp Ile Phe Gly Leu Asn Pro Ala Asp Glu Ser Thr Arg Ser Tyr Val
            1750                  1755                  1760

ATT TTA TCT TTT GAA AAC AAT GGT GAC TAC ATG GAC ATG AAG CAG GCT        2110
```

```
Ile Leu Ser Phe Glu Asn Asn Gly Asp Tyr Met Asp Met Lys Gln Ala
    1765                1770                1775

GAT ACT ACA CAG TAT GTC CCC ATG CTA GAA AGG AAA GAG GTT TCT AAA       2158
Asp Thr Thr Gln Tyr Val Pro Met Leu Glu Arg Lys Glu Val Ser Lys
    1780                1785                1790

TAT TCC GAC GTC CAG AGA TCA CTC TAT GAT CGT CCA GCC TCA TAT AAG       2206
Tyr Ser Asp Val Gln Arg Ser Leu Tyr Asp Arg Pro Ala Ser Tyr Lys
1795                1800                1805                1810

AAG AAA TCT ATG TTA GAC TCA GAA GTC AAA AAC CTC CTT TCA GAT GAT       2254
Lys Lys Ser Met Leu Asp Ser Glu Val Lys Asn Leu Leu Ser Asp Asp
                1815                1820                1825

AAC TCA GAA GGC CTT ACT TTA TTG GAT TTG TTG AGC TTC ACC TAT CAA       2302
Asn Ser Glu Gly Leu Thr Leu Leu Asp Leu Leu Ser Phe Thr Tyr Gln
    1830                1835                1840

GTT GCC CGA GGA ATG GAG TTT TTG GCT TCA AAA AAT TGT GTC CAC CGT       2350
Val Ala Arg Gly Met Glu Phe Leu Ala Ser Lys Asn Cys Val His Arg
    1845                1850                1855

GAT CTG GCT GCT CGC AAC GTC CTC CTG GCA CAA GGA AAA ATT GTG AAG       2398
Asp Leu Ala Ala Arg Asn Val Leu Leu Ala Gln Gly Lys Ile Val Lys
    1860                1865                1870

ATC TGT GAC TTT GGC CTG GCC AGA GAC ATC ATG CAT GAT TCG TTC TAT       2446
Ile Cys Asp Phe Gly Leu Ala Arg Asp Ile Met His Asp Ser Phe Tyr
1875                1880                1885                1890

GTG TCG AAA GGC AGT ACC TTT CTG CCC GTG AAG TGG ATG GCT CCT GAG       2494
Val Ser Lys Gly Ser Thr Phe Leu Pro Val Lys Trp Met Ala Pro Glu
                1895                1900                1905

AGC ATC TTT GAC AAC CTC TAC ACC ACA CTG AGT GAT GTC TGG TCT TAT       2542
Ser Ile Phe Asp Asn Leu Tyr Thr Thr Leu Ser Asp Val Trp Ser Tyr
                1910                1915                1920

GGC ATT CTG CTC TGG GAG ATC TTT TCC CTT GGT GGC ACC CCT TAC CCC       2590
Gly Ile Leu Leu Trp Glu Ile Phe Ser Leu Gly Gly Thr Pro Tyr Pro
                1925                1930                1935

GGC ATG ATG GTG GAT TCT ACT TTC TAC AAT AAG ATC AAG AGT GGG TAC       2638
Gly Met Met Val Asp Ser Thr Phe Tyr Asn Lys Ile Lys Ser Gly Tyr
    1940                1945                1950

CGG ATG GCC AAG CCT GAC CAC GCT ACC AGT GAA GTC TAC GAG ATC ATG       2686
Arg Met Ala Lys Pro Asp His Ala Thr Ser Glu Val Tyr Glu Ile Met
1955                1960                1965                1970

GTG AAA TGC TGG AAC AGT GAG CCG GAG AAG AGA CCC TCC TTT TAC CAC       2734
Val Lys Cys Trp Asn Ser Glu Pro Glu Lys Arg Pro Ser Phe Tyr His
                1975                1980                1985

CTG AGT GAG ATT GTG GAG AAT CTG CTG CCT GGA CAA TAT AAA AAG AGT       2782
Leu Ser Glu Ile Val Glu Asn Leu Leu Pro Gly Gln Tyr Lys Lys Ser
                1990                1995                2000

TAT GAA AAA ATT CAC CTG GAC TTC CTG AAG AGT GAC CAT CCT GCT GTG       2830
Tyr Glu Lys Ile His Leu Asp Phe Leu Lys Ser Asp His Pro Ala Val
                2005                2010                2015

GCA CGC ATG CGT GTG GAC TCA GAC AAT GCA TAC ATT GGT GTC ACC TAC       2878
Ala Arg Met Arg Val Asp Ser Asp Asn Ala Tyr Ile Gly Val Thr Tyr
    2020                2025                2030

AAA AAC GAG GAA GAC AAG CTG AAG GAC TGG GAG GGT GGT CTG GAT GAG       2926
Lys Asn Glu Glu Asp Lys Leu Lys Asp Trp Glu Gly Gly Leu Asp Glu
2035                2040                2045                2050

CAG AGA CTG AGC GCT GAC AGT GGC TAC ATC ATT CCT CTG CCT GAC ATT       2974
Gln Arg Leu Ser Ala Asp Ser Gly Tyr Ile Ile Pro Leu Pro Asp Ile
                2055                2060                2065

GAC CCT GTC CCT GAG GAG GAG GAC CTG GGC AAG AGG AAC AGA CAC AGC       3022
Asp Pro Val Pro Glu Glu Glu Asp Leu Gly Lys Arg Asn Arg His Ser
                2070                2075                2080
```

-continued

```
TCG CAG ACC TCT GAA GAG AGT GCC ATT GAG ACG GGT TCC AGC AGT TCC    3070
Ser Gln Thr Ser Glu Glu Ser Ala Ile Glu Thr Gly Ser Ser Ser Ser
        2085                2090                2095

ACC TTC ATC AAG AGA GAG GAC GAG ACC ATT GAA GAC ATC GAC ATG ATG    3118
Thr Phe Ile Lys Arg Glu Asp Glu Thr Ile Glu Asp Ile Asp Met Met
        2100                2105                2110

GAC GAC ATC GGC ATA GAC TCT TCA GAC CTG GTG GAA GAC AGC TTC CTG    3166
Asp Asp Ile Gly Ile Asp Ser Ser Asp Leu Val Glu Asp Ser Phe Leu
2115                2120                2125                2130

TAA CTG GCG GAT TCG AGG GTT CCT TCC ACT TCT                        3199
 *  Leu Ala Asp Ser Arg Val Pro Ser Thr Ser
                2135                2140
```

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
His Arg Asp Leu Ala Ala Arg Asn
1                   5
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 4..19
        (D) OTHER INFORMATION: /note= "Nucleotides 4 and 19 are
            "N" wherein "N" = G or C."

(ix) FEATURE:
        (A) NAME/KEY: misc_feature
        (B) LOCATION: 7..22
        (D) OTHER INFORMATION: /note= "Nucleotides 7, 10, 16 and
            22 are "N" wherein "N" = any of A, T, C, or G."

(xi) SEQUENCE DESCRIPTION: SEQ ID NO: 4:

```
GTTNCGNGCN GCCAGNTCNC GNTG                                          24
```